US007993349B2

(12) United States Patent
Hearn et al.

(10) Patent No.: US 7,993,349 B2
(45) Date of Patent: Aug. 9, 2011

(54) CRANIAL FLAP CLAMP INSTRUMENT

(75) Inventors: James P Hearn, Claymont, DE (US);
John H Manthorp, Downington, PA (US); Sean H Kerr, Collegeville, PA (US); Bryan Monro Armitage, Minneapolis, MN (US); Paul Burns, Perkasie, PA (US); Urs Wigger, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 2000 days.

(21) Appl. No.: 11/015,365

(22) Filed: Dec. 16, 2004

(65) Prior Publication Data
US 2005/0137608 A1    Jun. 23, 2005

Related U.S. Application Data

(63) Continuation-in-part of application No. 09/910,720, filed on Jul. 24, 2001, now Pat. No. 7,361,178.

(60) Provisional application No. 60/221,148, filed on Jul. 27, 2000.

(51) Int. Cl.
*A61B 17/58* (2006.01)
*A61B 17/84* (2006.01)
*A61F 2/00* (2006.01)
*A61F 2/08* (2006.01)

(52) U.S. Cl. ......................................... 606/99; 606/324

(58) Field of Classification Search .................. 606/151, 606/157, 213, 215, 216
See application file for complete search history.

(56) References Cited

U.S. PATENT DOCUMENTS

| 276,135 | A | 4/1883 | Cooley | |
|---|---|---|---|---|
| 460,222 | A | 9/1891 | Silsby | |
| 601,399 | A | 3/1898 | Manix | |
| 741,747 | A | 10/1903 | Walz | |
| 891,509 | A | 6/1908 | Tanner | |
| 1,918,700 | A | 7/1933 | Harris | |
| 2,118,561 | A | 5/1938 | Kleeberg | ........................ 85/37 |
| 2,275,058 | A | 3/1942 | Draving | |

(Continued)

FOREIGN PATENT DOCUMENTS
DE        1 089 116        9/1960
(Continued)

OTHER PUBLICATIONS

Chevalier, "Guide Du Dessinateur Industeriel", Edition 1984-1985, 7pages.

(Continued)

*Primary Examiner* — Anu Ramana
(74) *Attorney, Agent, or Firm* — Woodcock Washburn LLP

(57) ABSTRACT

The disclosed cranial flap clamp includes first and second clamping members and an extension member. A portion of the first member is positionable against inferior surfaces of a bone flap and skull and a portion of the second member is positionable against superior surfaces of the flap and skull. The extension member extends from the first member through the second member and fits between the flap and skull. Movement of either of the clamping members urges the inner surface of the first member against the inferior surfaces of the flap and skull and urges the inner surface of the second member against the superior surfaces of the flap and skull. The securing instrument includes features useful in cutting or crimping the extension member. The tension limiting assembly provides variable designs and combinations for limiting the tension placed on, and exerted by, the securing instrument during use.

83 Claims, 13 Drawing Sheets

U.S. PATENT DOCUMENTS

| | | | | |
|---|---|---|---|---|
| 2,291,413 A | 7/1942 | Siebrandt | | 128/83 |
| 2,315,326 A | 3/1943 | Gmeiner | | 128/340 |
| 2,316,297 A | 4/1943 | Southerland et al. | | 128/326 |
| 2,340,995 A | 2/1944 | Smith | | 128/321 |
| 2,485,531 A | 10/1949 | Dzus et al. | | 128/92 |
| 2,576,649 A | 11/1951 | Slind et al. | | |
| 3,038,626 A | 6/1962 | Simmons | | 29/243.522 |
| 3,175,556 A | 3/1965 | Wood et al. | | 128/305 |
| 3,259,383 A | 7/1966 | Johnson | | |
| 3,507,284 A | 4/1970 | Simmons et al. | | 128/318 |
| 3,971,384 A | 7/1976 | Hasson | | 128/335 |
| 4,050,464 A | 9/1977 | Hall | | |
| 4,088,134 A | 5/1978 | Mazzariello | | 128/321 |
| 4,452,246 A | 6/1984 | Bader et al. | | 128/340 |
| 4,644,953 A | 2/1987 | Lahodny et al. | | 128/305 |
| 4,669,473 A | 6/1987 | Richards et al. | | 128/334 |
| 4,763,669 A | 8/1988 | Jaeger | | 128/751 |
| 4,889,110 A | 12/1989 | Galline et al. | | 606/69 |
| 4,950,284 A | 8/1990 | Green et al. | | 606/216 |
| 5,030,050 A | 7/1991 | Auriol et al. | | 411/38 |
| 5,059,193 A | 10/1991 | Kuslich | | 606/61 |
| 5,098,433 A | 3/1992 | Freedland | | 606/63 |
| 5,250,049 A | 10/1993 | Michael | | 606/72 |
| 5,258,015 A | 11/1993 | Li et al. | | 606/232 |
| 5,282,807 A | 2/1994 | Knoepfler | | 606/143 |
| 5,339,870 A * | 8/1994 | Green et al. | | 140/123.5 |
| 5,342,393 A | 8/1994 | Stack | | 606/213 |
| 5,388,619 A * | 2/1995 | Ghawi | | 140/123.6 |
| 5,392,822 A | 2/1995 | Kraus | | 140/123.6 |
| 5,468,242 A | 11/1995 | Reisberg | | |
| 5,538,427 A | 7/1996 | Hoffman et al. | | |
| 5,800,436 A | 9/1998 | Lerch | | |
| 5,814,048 A | 9/1998 | Morgan | | |
| 5,893,850 A | 4/1999 | Cachia | | 606/72 |
| 5,935,133 A | 8/1999 | Wagner et al. | | 606/103 |
| 6,021,553 A | 2/2000 | Bieber et al. | | 29/243.521 |
| 6,022,351 A * | 2/2000 | Bremer et al. | | 606/324 |
| 6,068,631 A | 5/2000 | Lerch | | |
| 6,123,711 A | 9/2000 | Winters | | |
| 6,126,663 A | 10/2000 | Hair | | |
| 6,168,596 B1 | 1/2001 | Wellisz et al. | | |
| 6,228,087 B1 | 5/2001 | Fenaroli et al. | | |
| 6,241,732 B1 | 6/2001 | Overaker et al. | | |
| 6,328,743 B2 | 12/2001 | Lerch | | |
| 6,361,538 B1 | 3/2002 | Fenaroli et al. | | |
| 6,371,958 B1 | 4/2002 | Overaker | | |
| 6,379,363 B1 | 4/2002 | Herrington et al. | | 606/79 |
| 6,485,493 B1 | 11/2002 | Bremer | | |
| 6,751,841 B2 | 6/2004 | Schnabel et al. | | 29/524.1 |
| 2001/0049529 A1 | 12/2001 | Cachia et al. | | 606/72 |
| 2002/0004661 A1 | 1/2002 | Sevrain et al. | | 606/73 |
| 2002/0016593 A1 | 2/2002 | Hearn et al. | | 606/72 |
| 2002/0029042 A1 | 3/2002 | Fenaroli et al. | | 606/73 |
| 2002/0040224 A1 | 4/2002 | Lerch | | 606/72 |
| 2002/0062128 A1 | 5/2002 | Amis | | 606/72 |
| 2002/0095156 A1 | 7/2002 | Kuras et al. | | 606/72 |
| 2002/0120274 A1 | 8/2002 | Overaker et al. | | 606/72 |
| 2002/0120281 A1 | 8/2002 | Overaker | | 606/151 |

FOREIGN PATENT DOCUMENTS

| | | |
|---|---|---|
| DE | 19634697 | 4/1998 |
| DE | 19634699 | 4/1998 |
| DE | 29812988 | 9/1998 |
| DE | 29812989 | 9/1998 |
| DE | 19832798 | 11/1999 |
| DE | 19832798 C1 | 11/1999 |
| DE | 19952359 | 3/2001 |
| DE | 20101793 | 5/2001 |
| DE | 20109893 | 8/2001 |
| DE | 20109894 | 9/2001 |
| EP | 0 857 466 A1 | 8/1998 |
| EP | 0857466 A1 | 8/1998 |
| EP | 867149 | 9/1998 |
| EP | 1303223 B1 | 7/2001 |
| EP | 1154724 A1 | 11/2001 |
| FR | 2777449 A1 | 10/1999 |
| GB | 744614 C | 1/1944 |
| JP | 9206311 A | 8/1997 |
| JP | 2000135230 A | 5/2000 |
| JP | 2002045367 | 2/2002 |
| JP | 2002065686 | 3/2002 |
| SU | 1419690 A | 8/1988 |
| SU | 1600713 A1 | 10/1990 |
| WO | WO 98/46153 | 10/1998 |
| WO | WO 02/09602 A1 | 2/2002 |

OTHER PUBLICATIONS

Estin et al., "Bone Flap Fixation with Titanium Clamps: A New Technique," Surgical Neurology, 2000, vol. 53, pp. 391-395.

In the United States Patent and Trademark Office, In Re. U.S. Appl. No. 09/910,720, filed Jul. 24, 2004: Office Action dated Jan. 24, 2006.

Lusuardi AG, In Re. EP Patent Application 01933533.0/1265 filed Jun. 7, 2001, EP Response dated Apr. 8, 2003, 2 pages.

Summons of Lusuardi, Werther, Dr. Lusuardi AG to attend oral proceedings pursuant to Rule 115(1) EPC, Regarding EP Patent Application No. 01933533.0-1265, EP Patent No. 1303223, European Patent Office, Jun. 29, 2010, 9 pages.

* cited by examiner

A-A

B-B

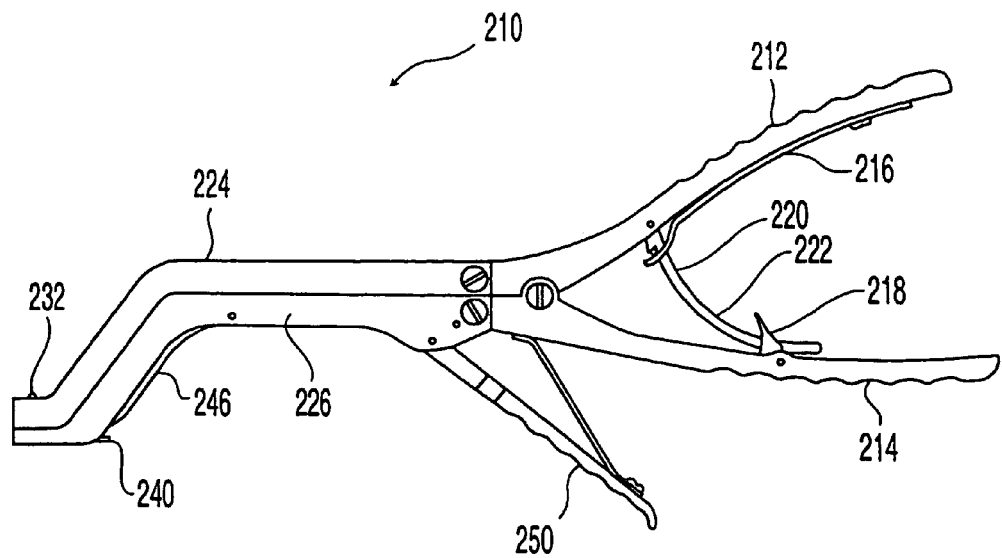
Fig. 12
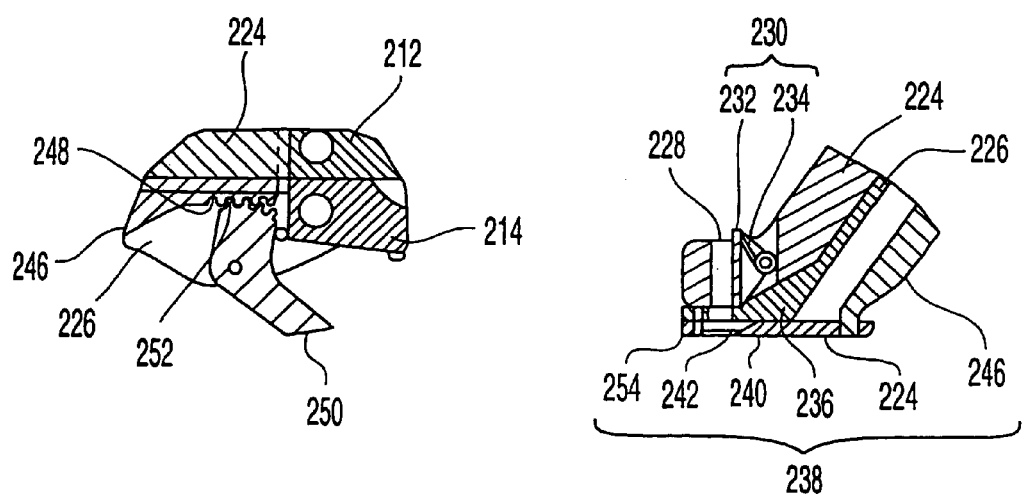
Fig. 14
Fig. 13

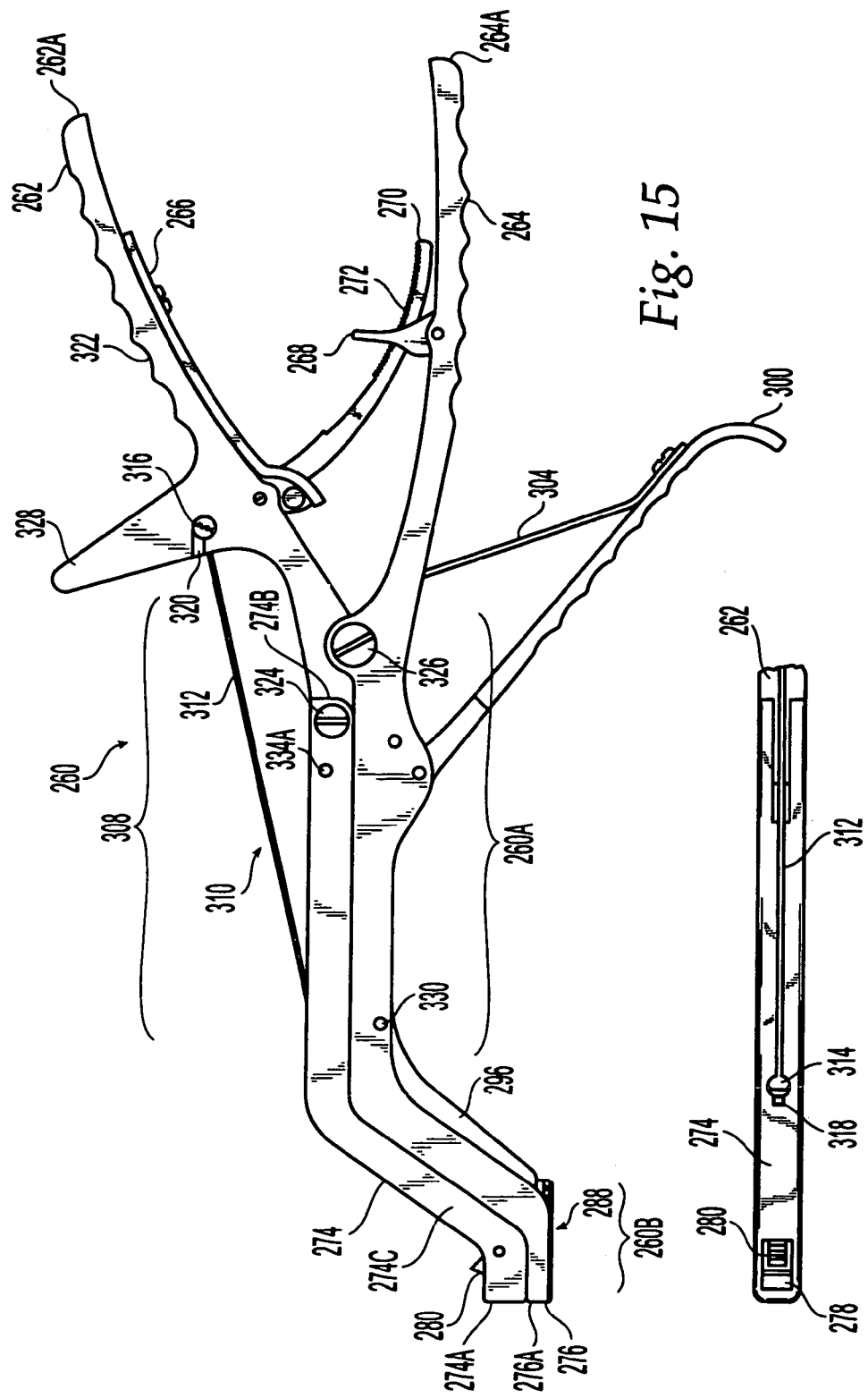

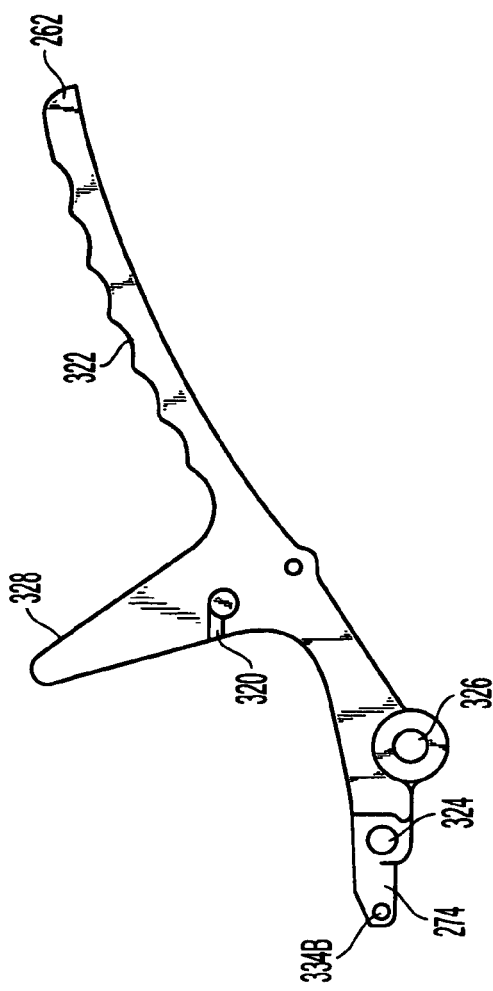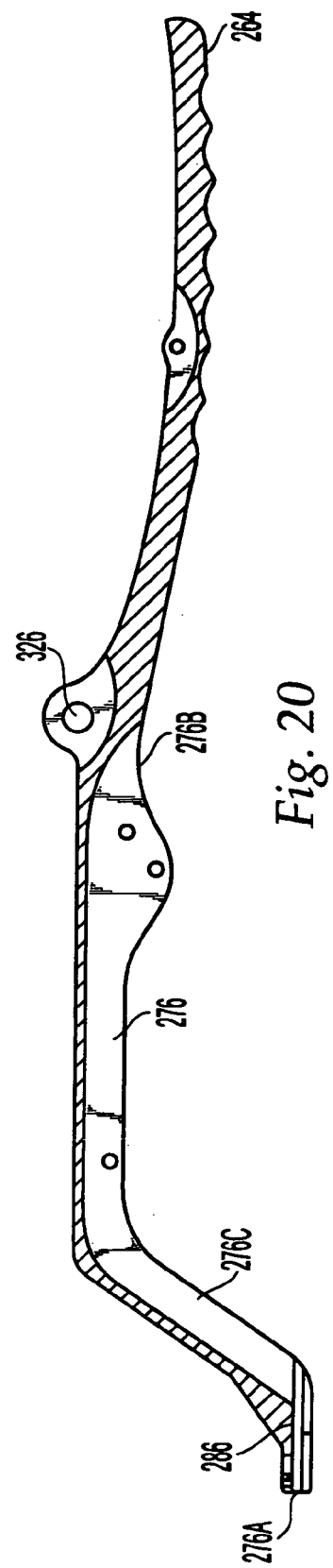
Fig. 19
Fig. 20

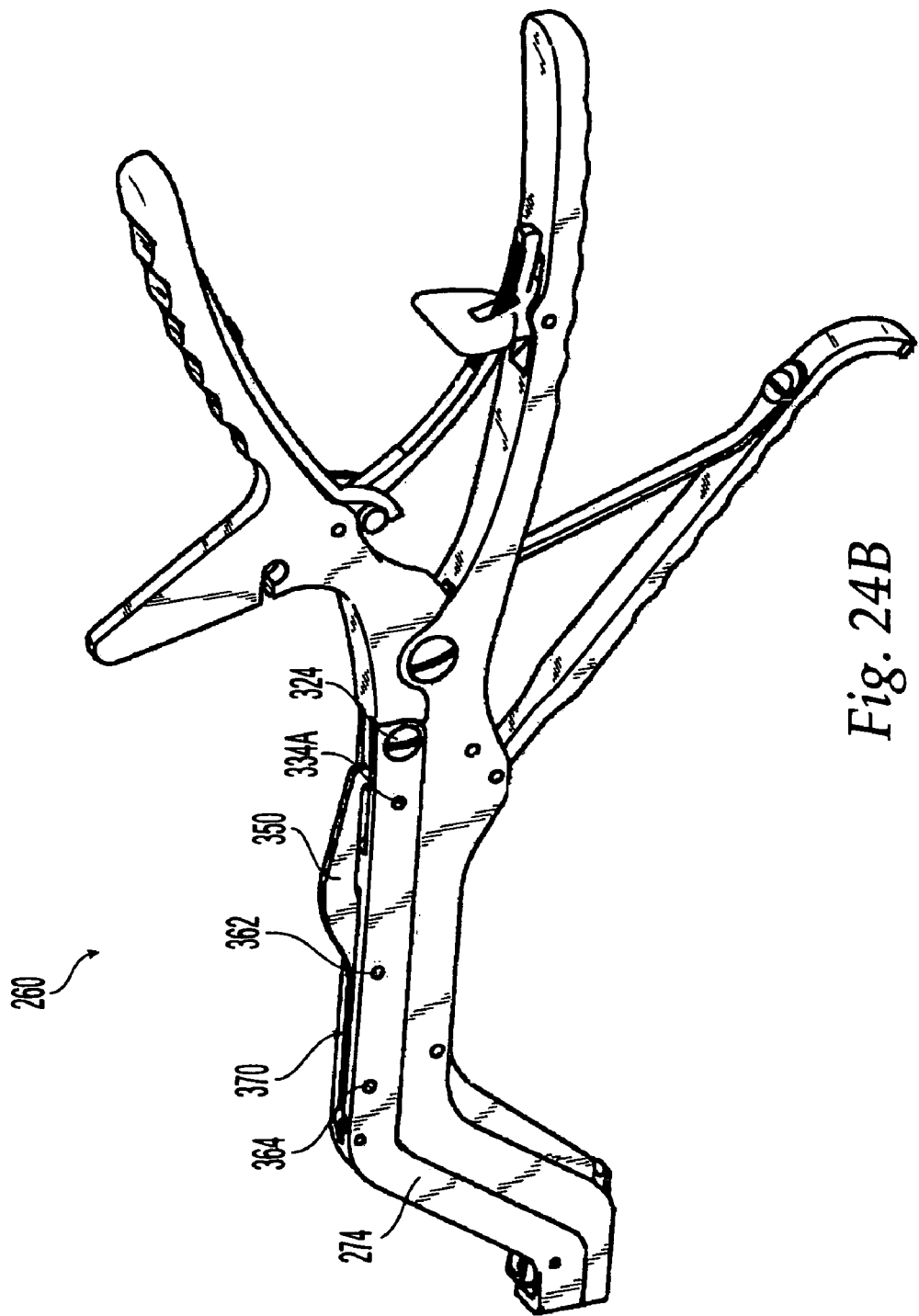

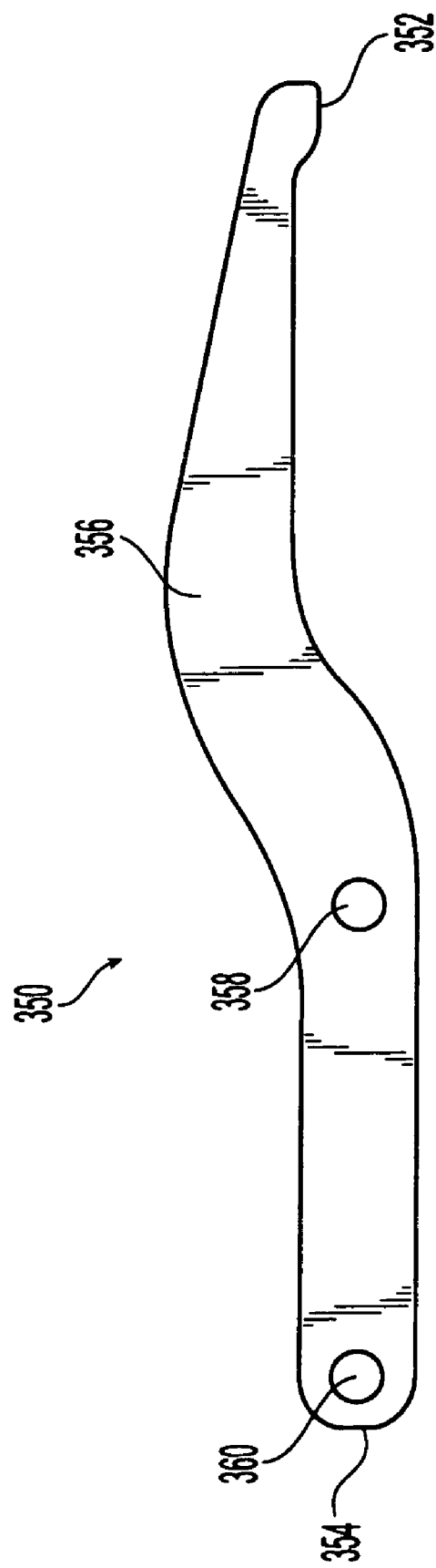

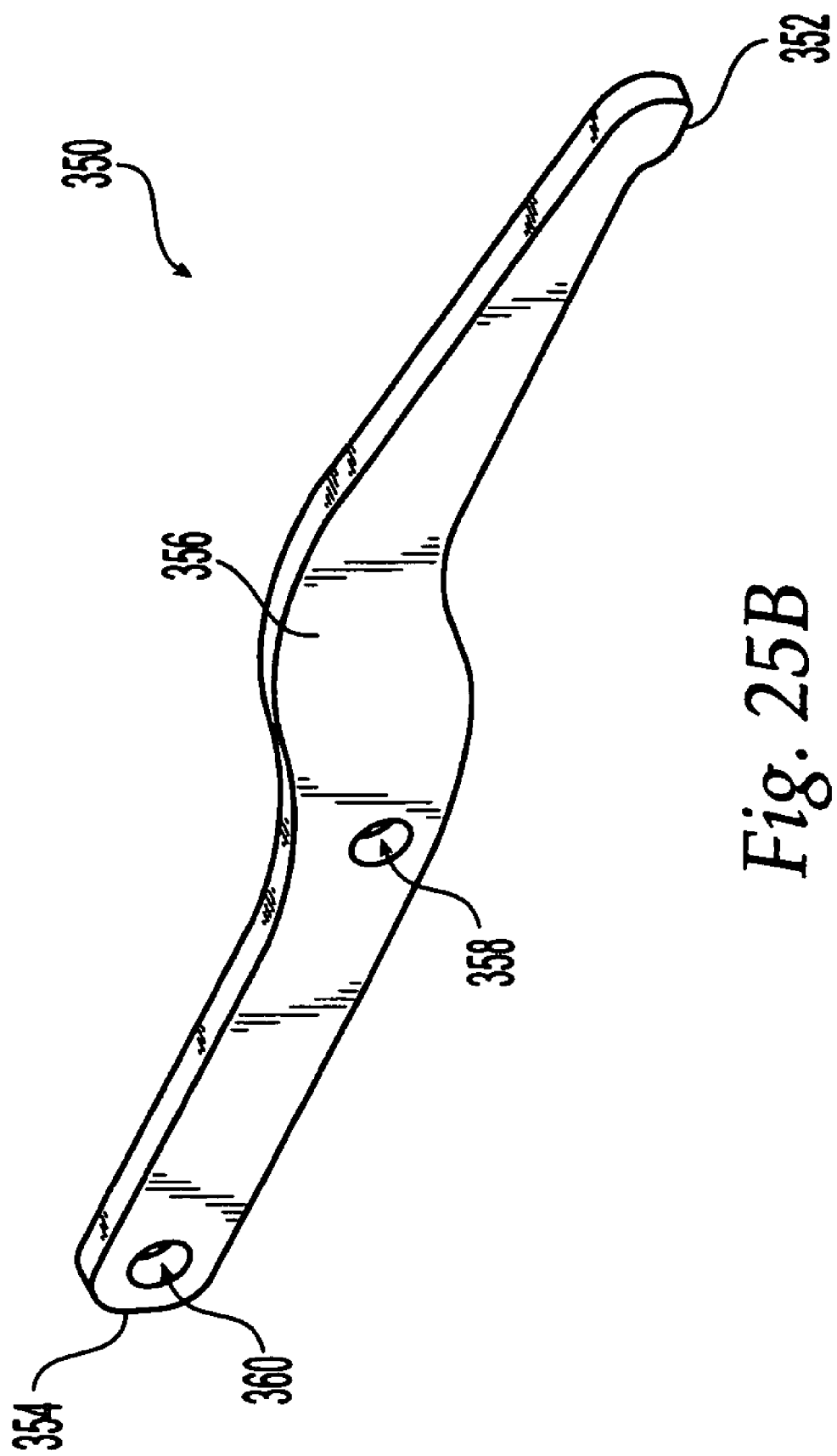

CRANIAL FLAP CLAMP INSTRUMENT

CROSS-REFERENCE TO RELATED APPLICATIONS

This is a continuation-in-part of U.S. Non-Provisional patent application Ser. No. 09/910,720, filed Jul. 24, 2001 now U.S. Pat. No. 7,361,178, which claims the benefit under 35 U.S.C. §119(e) of U.S. Provisional Patent Application No. 60/221,148, filed Jul. 27, 2000, the entirety of which applications are expressly incorporated herein by reference thereto.

FIELD OF THE INVENTION

The present invention is directed to an instrument for use with a cranial flap clamp for attaching a bone flap to a skull.

BACKGROUND OF THE INVENTION

Craniotomies are surgical procedures performed in the treatment of various brain problems, such as tumors, aneurysms, blood clots, head injuries, abscesses, and the like. During a craniotomy procedure, access to the brain is achieved by the creation of a hole in the bone that defines the skull. The hole or "window" in the skull is usually created by identifying the area of the brain to which access is needed, drilling several holes into the skull near the periphery of this area, inserting a cutting tool into one of the holes, and making cuts from one hole to another. Removing the cut-out area of the skull, generally referred to as a bone flap, allows the desired access to the brain.

If all of the drilled holes are joined by cuts, such that the cuts form a complete outline of the "window", then the bone flap can simply be removed. Alternatively, if the cuts form only a partial outline of the window, the bone flap can be bent out of the way, in a hinge-like manner. Although the size and shape of the bone flap will vary with the desired cranial access area and size, a typical bone flap would be generally rectangular in shape and approximately four by six centimeters.

After the desired medical or surgical procedure on the brain has been performed, the bone flap must be replaced and held in a stable position to allow the skull to heal. There are many methods available for affixing the bone flap to the skull. One general method, for example, requires drilling pairs of holes in the edges of the skull and bone flap, threading wire through the holes, and twisting or tying the ends of the wire together to secure the edges of the bone flap to the skull. Disadvantages of this method include the tedious nature and length of time required for the procedure and the possibility of injury from drilling the holes too deep or from the sharp ends of the wires.

Another method of fixation generally involves the use of bone plates which are secured across the gaps between the bone flap and skull by screws. The disadvantages associated with the use of plates and screws relate to the undesirable cosmetic appearance resulting from the protrusion of the plate and screw above the bone surface. As there is minimal intervening soft tissue between the skull and the skin, unappealing external appearance is particularly a problem. The lack of soft tissue also has the unwanted consequence of permitting the patient to feel the plate and screw simply by pressing on the scalp. Thus, there is a need for improved devices for fixing a bone flap to a skull.

SUMMARY OF THE INVENTION

An embodiment of a securing instrument for a cranial flap clamp is described, comprising: first and second handles pivotally associated with each other; a gripping arm, and a tensioning arm, the gripping arm operatively associated with the first handle and the tensioning arm operatively associated with the second handle; the gripping and tensioning arms being movable in response to movement of the first and second handles; the gripping and tensioning arms each further having proximal and distal portions, the distal portions having a recess extending therethrough for receiving an extension member of the cranial flap clamp; a clamping assembly operatively associated with the recess and having an inactive configuration in which the clamping assembly allows the extension member to slide in the recess, and an active configuration in which the assembly fixes the extension member in the recess; and a crimping element operatively associated with at least one of the gripping and tensioning arms for crimping the extension member, the crimping element further having first and second crimping members; wherein squeezing the first and second handles together configures the clamping assembly to the active configuration.

The clamping element may also have a clamp rotatably coupled to the gripping arm, such that separating the gripping and tensioning arms rotates the clamp within the recess and moves the clamping element from the inactive configuration to the active configuration.

The securing instrument may also comprise a resilient member disposed between the first and second handles for biasing the clamping element in the active configuration when the gripping and tensioning arms are separated.

The tensioning arm may further comprise a foot operative to maintain the clamping elements in the inactive configuration when the gripping and tensioning arms are in contact. The foot may include a ramped surface for engaging the clamping element to fix the extension member within the recess.

The distal portion of the tensioning arm further may also include a grooved end, and the crimping assembly may further comprise: a slider having a crimping edge for crimping the extension member, and sides configured and dimensioned for sliding engagement with the grooved end of the tensioning arm; a link operatively associated with the tensioning arm for sliding movement with respect thereto, the link having a distal end coupled to the slider and a proximal end comprising teeth; and a lever rotatably coupled with the tensioning arm, the lever having a proximal gripping portion and a distal portion comprising teeth configured to engage the teeth of the link; wherein moving the lever in a first direction with respect to the tensioning arm causes the crimping edge of the slider to crimp an extension member placed therein. The crimping assembly may further include a cutting stop, the cutting stop configured to cooperate with the crimping edge of the slider to at least crimp the extension member.

The gripping arm may further comprise an intermediate portion located between the gripping arm proximal and distal portions, the gripping arm proximal portion associated with the distal portion of the first handle, the distal portion of the gripping arm extending from the intermediate portion substantially parallel to the proximal portion, and the intermediate portion angled with respect to the gripping arm proximal and distal portions, and the tensioning arm may further comprise an intermediate portion located between the tensioning arm proximal and distal portions; the tensioning arm proximal portion associated with the distal portion of the second handle, the distal portion of the tensioning arm extending from the intermediate portion substantially parallel to the proximal portion, and the intermediate portion angling from the tensioning arm proximal portion; wherein the intermediate portions of the gripping and tensioning arms are oriented substantially parallel when the instrument is in the inactive configuration.

The securing instrument may further comprise a resilient element associated with the first and second handles to bias the first and second handles away from each other. The securing instrument may further comprise a locking bar having a first end pivotably coupled to the first handle and a curved body portion with a plurality of teeth; and a locking clip pivotably coupled to the second handle and having a through channel, wherein the locking clip is movable between a free position in which the locking bar is moveable within the channel and a ratchet position in which the teeth of the locking bar engage a surface of the channel to prohibit the locking bar from moving with respect to the channel, thereby locking the relative positions of the first and second handles with respect to each other.

The securing instrument may still further comprise a tension limiting assembly, comprising an extensible tension element having first and second ends, the first end releasably attachable to the first handle at a first location and the second end releasably attachable to the gripping arm; wherein the first handle and the gripping arm are connected at a pivot joint. The first and second ends of the extensible tension element may engage the first handle and the gripping arm to allow the handle and arm to pivot with respect to each other in a first direction and to resist pivoting in the opposite direction. The tension element may resist pivoting of the handle and arm in the first direction until about 15 newtons (N) is applied to the distal portion of the gripping arm via the handles. When a force greater than about 15 N is applied via the handles to the distal portion of the gripping arm, the tension element may stretch to allow the handle and arm to pivot in the first direction. Further force applied to the handles may cause the tension element to stretch, with substantially no additional force transmitted to the cranial flap clamp.

The tension element may comprise a nitinol wire having a diameter of from about 0.25 mm to about 2.5 mm. The nitinol wire may have a maximum strain of about 5% to about 11% before rupture.

At least one of the first and second ends of the tension element may comprise a ball end. At least one of the first and second ends of the tension element may comprise a pin end.

The securing instrument may further comprise a second tension element having first and a second ends, each end having an attachment element, wherein the first end is attachable at the first handle and the second end is attachable to the gripping arm. At least one tension element may comprise a nitinol wire. The first and second tension elements may have substantially different compositions, substantially different tensile strengths, and/or substantially different cross-section diameters.

A kit for use with a cranial flap clamp is also described, comprising: the securing instrument as described herein, a plurality of tension elements, each tension element having first and second ends, the first end having an attachment element for engaging the first arm and the second end having an attachment element for engaging the gripping arm; wherein at least two of the plurality of tension elements have force/strain ratios that are substantially unequal.

At least one tension element may comprise a nitinol wire. At least two of the plurality of tension elements may be comprised of substantially the same material. At least one of the plurality of tension elements may comprise a nitinol wire and a second of the plurality of tension elements comprises a constant-force spring. At least two of the plurality of tension elements may have substantially different tensile strengths.

Another embodiment of a securing instrument for a cranial flap clamp is described, comprising: a first handle associated with a first clamping arm and a second handle associated with a second clamping arm, the first and second handles being pivotally connected; the first and second clamping arms each further having a distal portion, the distal portions each further configured to receive at least a portion of an extension element of the cranial flap clamp; an extension element-clamping assembly operatively associated with the recess of at least the first clamping arm; the assembly configured to selectively engage the extension element; and a clamp-engaging surface associated with the second clamping arm, the clamp-engaging surface configured to contact a clamp surface of the cranial flap clamp; wherein when the extension element-clamping assembly engages the extension element and the clamp-engaging surface contacts the clamp surface, moving the handles with respect to each other causes the extension element and the clamp surface to move with respect to each other.

The securing instrument may further comprise a crimping assembly associated with the second arm and configured to at least partially deform the extension element. The crimping assembly may further comprise first and second crimping members disposed near the distal end of the second arm and configured to actuate when the first and second handles are urged together.

Moving the first and second handles together may cause the extension element engaging assembly to engage the extension element.

The crimping assembly may further include a cutting element configured to cooperate with at least one of the crimping members to at least crimp the extension member.

The extension element-engaging clamping assembly may further comprise a gripping element disposed within the recess of the first clamping arm, and rotatably coupled to the first clamping arm such that moving the first and second handles rotates the gripping element within the recess to selectively engage the extension element.

The first and second arms may further comprise a handle-engaging portion associated with the first and second handles, respectively, and an intermediate portion disposed between the handle-engaging and distal portions, the intermediate portions oriented at an oblique angle with respect to their respective distal portions.

The securing instrument may further comprise a tension limiting assembly, comprising an extensible tension element having first and second ends, the first end releasably attachable to the first handle at a first location and the second end releasably attachable to the first clamping arm; wherein the first clamping arm is pivotably associated with the first handle.

The first clamping arm and first handle may be connected via a pivot joint, wherein the first and second ends of the extensible tension element engage the first handle and the first clamping arm to allow the handle and arm to pivot with respect to each other in a first direction about the pivot joint and to resist pivoting in the opposite direction about the pivot joint.

The tension element may resist pivoting of the handle and arm in the first direction until about 15 N is applied to the distal portion of the gripping arm via the handles. When a force greater than about 15 N is applied via the handles to the distal portion of the gripping arm, the tension element may stretch to allow the handle and arm to pivot in the first direction. Further force applied to the handles may cause the tension element to stretch, with substantially no additional force transmitted to the cranial flap clamp. The tension element comprises a nitinol wire. The nitinol wire may have a diameter of from about 0.25 mm to about 2.5 mm. The nitinol wire may have a maximum strain of about 5% to about 11% before rupture.

At least one of the first and second ends of the tension element may comprise a ball end. At least one of the first and second ends of the tension element may comprise a pin end.

The tension limiting assembly may further comprise a second tension element having first and a second ends, each end having an attachment element, wherein the first end is attachable at the first handle and the second end is attachable to the first clamping arm. At least one tension element may comprise a nitinol wire. The first and second tension elements may have substantially different compositions, and/or substantially different tensile strengths.

An embodiment of a cranial flap clamp system is also described, comprising: at least one cranial flap clamp comprising first and second skull clamping elements and an extension element configured to connect the clamping elements; a cranial flap clamp installation instrument comprising: a first handle associated with a first clamping arm and a second handle associated with a second clamping arm, the first and second handles being pivotally connected, the first and second clamping arms each further having a distal portion, the distal portions each further configured to receive at least a portion of an extension element of the cranial flap clamp; an extension element-clamping assembly operatively associated with the recess of at least the first clamping arm; the assembly configured to selectively engage the extension element; and a clamp-engaging surface associated with the second clamping arm, the clamp-engaging surface configured to contact one of the first and second skull clamping elements; wherein when the extension element-clamping assembly engages the extension element and the clamp-engaging surface contacts the clamp surface, moving the handles with respect to each other causes the extension element and the clamp surface to move with respect to each other.

The securing instrument may further comprise a crimping assembly associated with the second arm and configured to at least partially deform the extension element. The crimping assembly may further comprising a slider having a crimping edge, the crimping edge configured to crimp an extension member placed within the recess.

Moving the first and second handles together may cause the extension element engaging assembly to engage the extension element.

The crimping assembly further may include a cutting element configured to cooperate with at least one of the crimping members to at least crimp the extension member.

The extension element-engaging clamping assembly may further comprise a gripping element disposed within the recess of the first clamping arm, and rotatably coupled to the first clamping arm such that moving the first and second handles rotates the gripping element within the recess to selectively engage the extension element.

The first and second arms may further comprise a handle-engaging portion associated with the first and second handles, respectively, and an intermediate portion disposed between the handle-engaging and distal portions, the intermediate portions oriented at an oblique angle with respect to their respective distal portions.

The securing instrument may further comprise a tension limiting assembly, comprising an extensible tension element having first and second ends, the first end releasably attachable to the first handle at a first location and the second end releasably attachable to the first clamping arm; wherein the first clamping arm is pivotably associated with the first handle.

The first clamping arm and first handle may be connected via a pivot joint, wherein the first and second ends of the extensible tension element engage the first handle and the first clamping arm to allow the handle and arm to pivot with respect to each other in a first direction about the pivot joint and to resist pivoting in the opposite direction about the pivot joint.

At least a portion of the cranial flap clamp may be comprised of a bioresorbable material.

The tension element may resist pivoting between the handle and arm in the first direction until about 15 N is applied between the distal portions of the gripping and tensioning arms using the handles.

When about 15 N is applied between the distal portions of the gripping and tensioning arms, further movement of the handles together may cause the tension element to stretch, with substantially no additional force transmitted to the cranial flap clamp. When a force greater than about 15 N is applied via the handles between the distal portions of the gripping and tensioning arms, the tension element may stretch to allow the handle and arm to pivot in the first direction.

At least a portion of the cranial flap clamp may be comprised of metal, and the metal may be titanium.

The tension limiting assembly may further comprise a second tension element having first and a second ends, each end having an attachment element, wherein the first end is attachable at the first handle and the second end is attachable to the first clamping arm.

A method for installing a cranial flap clamp in a patient is also described, comprising the steps of: (a) providing a cranial flap clamp having first and second clamp elements configured to clamp first and second bone segments, and an extension element fixed to the first clamp element and engageable with the second clamp element; (b) providing a tensioning instrument having first and second arms configured to engage one of the clamp elements and the extension element; (c) positioning the first and second clamps to sandwich the first and second bone segments therebetween; (d) positioning the first arm adjacent the second clamp element and positioning the second arm adjacent the extension element; (e) moving the first and second arms with respect to each other to a first position to engage the extension element and the second clamp element; (f) moving the first and second arms with respect to each other to a second position to move the extension element with respect to the second clamp element to thereby clamp the first and second bone segments between the first and second clamp elements; (g) moving the first and second arms with respect to each other to a third position to fix the extension element to the second clamp element; and (h) disengaging the instrument from the cranial flap clamp.

The instrument may further comprise first and second handles pivotably connected, the first and second handles each having a proximal user end and a distal end configured to engage a respective first or second arm. The instrument may further comprise a crimping assembly associated with the second arm and configured to at least partially deform the extension element to fix the extension element to the second clamp element.

The crimping assembly may further comprise: a lever pivotably connected to the second arm, a slider slidably engaged with a distal end of the second arm, the lever and slider operatively associated with each other by corresponding sets of teeth; the slider further comprising a crimping edge wherein when the lever is pivoted in a first direction with respect to the second arm, the crimping edge crimps the extension element.

The instrument further may comprise a tension limiting assembly disposed between the first arm and the first handle, the assembly configured to limit the tension applied between the first and second clamp elements to a predetermined maximum amount, regardless of the force applied between the first and second handles. The tension limiting assembly may further comprise a pivot joint and a tensioning element, the pivot joint connecting the first arm and the first handle, and the tensioning element having a first end configured to engage the first arm and a second end configured to engage the first handle.

The pivot joint further may have a pivot axis, the pivot joint and tensioning element configured to allow the handle and arm to pivot about the axis in a first direction and to resist pivoting about the axis in a second direction.

The tensioning element may be configured to allow the handle and arm to pivot about the axis in the second direction when the handle and arm are subjected to a predetermined maximum force. The tensioning element may comprise a wire, and the wire may be made of nitinol. The tensioning element may comprise a spring.

BRIEF DESCRIPTION OF THE DRAWINGS

FIG. 12 is side view of a securing instrument for use with the cranial flap clamp according to the present invention;

FIG. 13 is a cross sectional view of the distal portion of the securing instrument of FIG. 12; and FIG. 14 is a cross sectional view of the proximal portion of the gripping arm of the securing instrument of FIG. 12.

FIG. 15 is a side view of another embodiment of a securing instrument for use with the cranial flap clamp according to the present invention;

FIG. 16 is a top view of a forward portion of the instrument of FIG. 15;

FIG. 19 is a side view of the upper handle of the instrument of FIG. 15;

FIG. 20 is a cross sectional view of the lower handle of the instrument of FIG. 15;

FIG. 24B is a perspective view of the instrument of FIG. 24A;

FIG. 25A is a side view of a cantilever beam for use with the instrument of FIG. 24A-24B; and FIG. 25B is a perspective view of the cantilever beam of FIG. 25A.

DETAILED DESCRIPTION OF THE PREFERRED EMBODIMENTS

Figure 1:
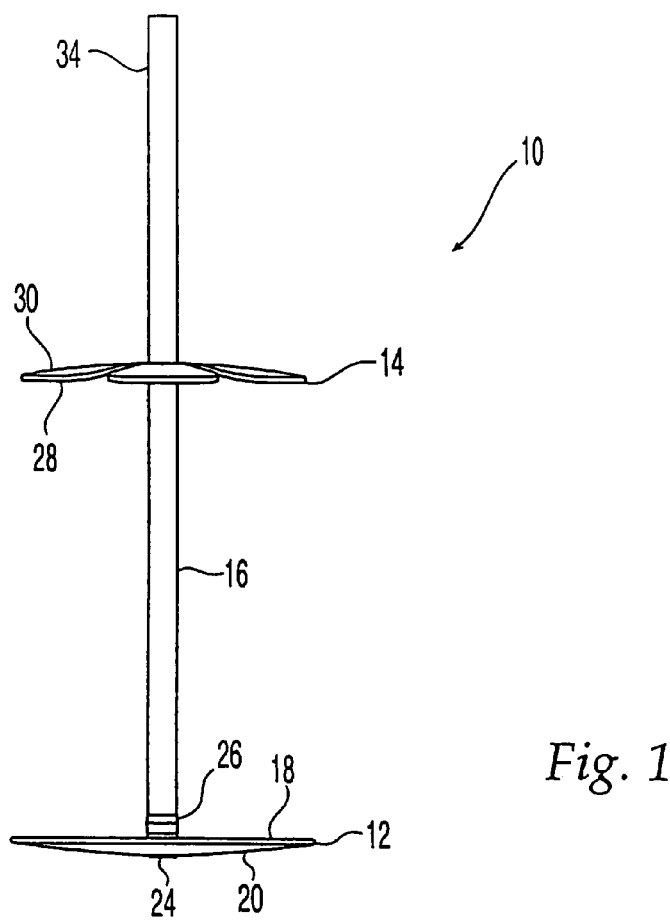
FIG. 1 is a perspective view of one embodiment of a cranial flap clamp according to the present invention.
Figure 2:
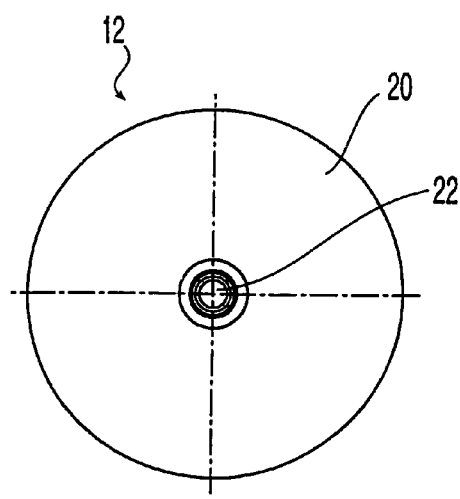
FIG. 2 is a top view of the outer surface of a first clamping member.

As shown in FIGS. 1-4, one embodiment of a cranial flap clamp 10 according to the present invention includes a first clamping member 12, a second clamping member 14, and an extension member 16. Cranial flap clamp 10 can be made of any suitable biocompatible material, such as stainless steel, titanium, a titanium based alloy, or a resorbable material. If cranial flap clamp 10 is made of a metallic material, preferably first and second clamping members 12, 14 and extension member 16 are made of the same material to minimize the potential for galvanic corrosion. First clamping member 12 has a disk shape with a concave inner surface 18 and a convex outer surface 20. Extension member 16 extends from inner surface 18 of first clamping member 12. Although extension member 16 is shown as a tube, extension member 16 can be any similar structure so long as the structure and material allow crimping, as explained below.

Extension member 16 can be integral to first clamping member 12. Alternatively, extension member 16 can be fastened to first clamping member 12 using any number of known ways. For example, first clamping member 12 can be provided with a bore 22 through which extension member 16 is inserted. A head 24 engages edges of bore 22 to prevent first clamping member 12 from sliding off extension member 16. Extension member 16 can be provided with an enlarged portion 26 near inner surface 18 of first clamping member 12 to prevent movement of first clamping member 12 along extension member 16 in a direction away from head 24. Enlarged portion 26 can be created, for example, by crimping. Alternatively, a ferrule or other similar component can be placed on extension member 16.

Second clamping member 14 also has a disk shape with a concave inner surface 28 and a convex outer surface 30. Second clamping member 14 is provided with an opening 32 through inner and outer surfaces 28, 30 for slidably receiving extension member 16. Because opening 32 slidably receives extension member 16, opening 32 and extension member 16 preferably have complimentary shapes. For example, if extension member 16 is a tube, then opening 32 preferably has a substantially circular shape. In order to prevent second clamping member 14 from sliding off extension member 16, extension member 16 can be provided with a flared proximal portion 34.

Figure 4:
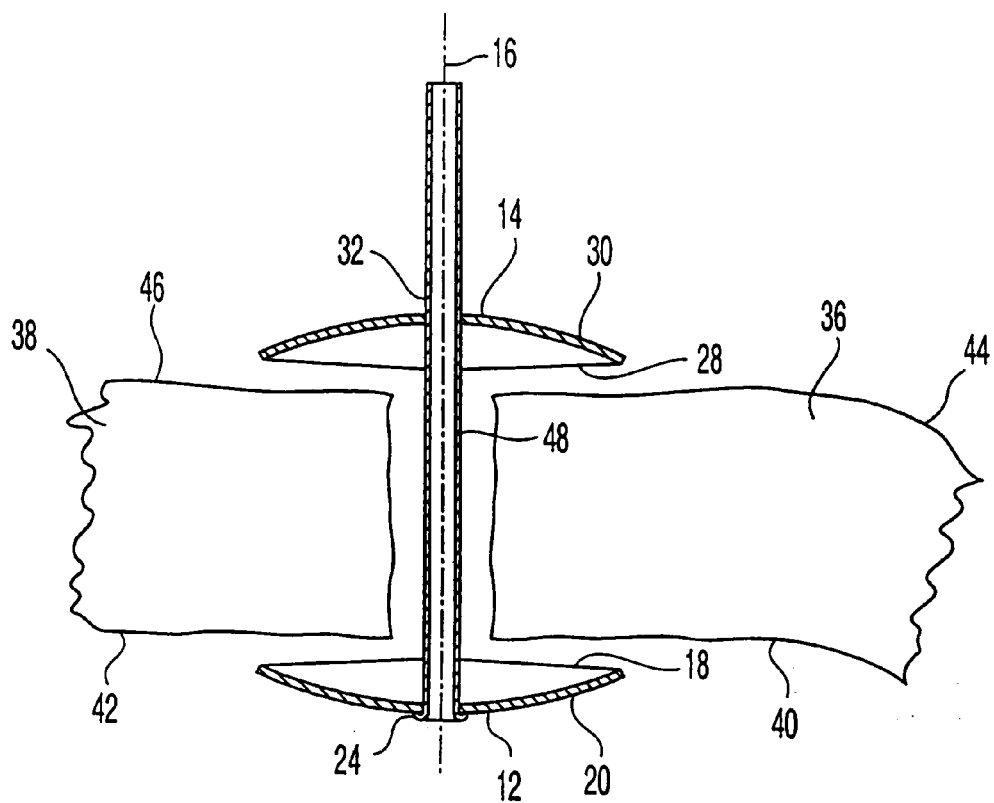
FIG. 4 is a cross sectional view of the cranial flap clamp of FIG. 1 implanted between a skull and a bone flap prior to crimping and cutting of the extension member.

In use, cranial flap clamp 10 fixes a bone flap 36 to a skull 38. FIG. 4 shows cranial flap clamp 10 in a first position. At least a portion of inner surface 18 of first clamping member 12 abuts an inferior surface 40 of bone flap 36 and an inferior surface 42 of skull 38. At least a portion of inner surface 28 of second clamping member 14 abuts a superior surface 44 of bone flap 36 and an superior surface 46 of skull 38. A portion of extension member 16 fits in a saw gap 48 between bone flap 36 and skull 38.

Figure 5:
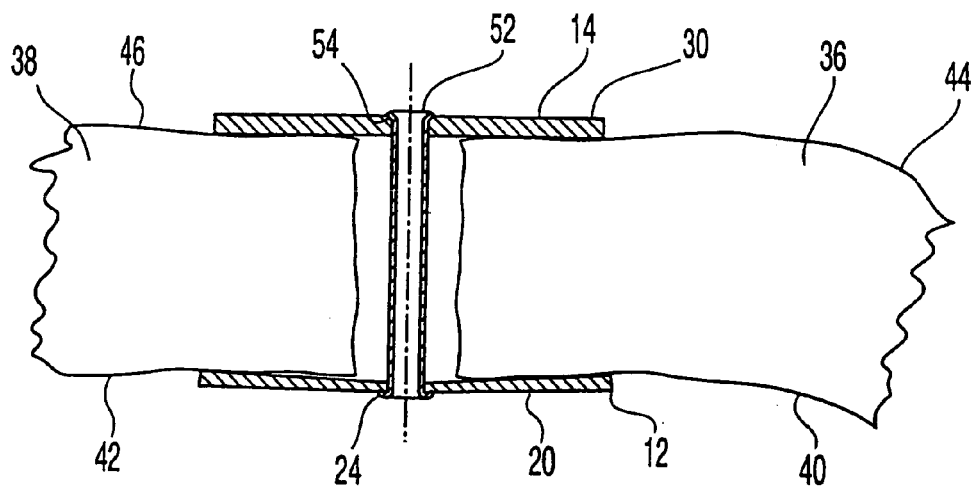
FIG. 5 is a cross sectional view of the cranial flap clamp of FIG. 4 after crimping and cutting of the extension member.

FIG. 5 shows cranial flap clamp 10 in a second position with first and second clamping member 12, 14 located more proximally to each other than the first position of FIG. 4. This movement (which can result from the movement of either or both of first and second clamping members 12, 14) urges inner surface 18 of first clamping member 12 against inferior surfaces 40, 42 of bone flap 36 and skull 38 and inner surface 28 of second clamping member 14 against superior surfaces 44, 46 of bone flap 36 and skull 38. There are a number of ways to move cranial flap clamp 10 from first position to second position. For example, extension member 16 can be pulled up while second clamping member 14 is pushed down. An instrument for performing these functions is described below.

Figure 3:
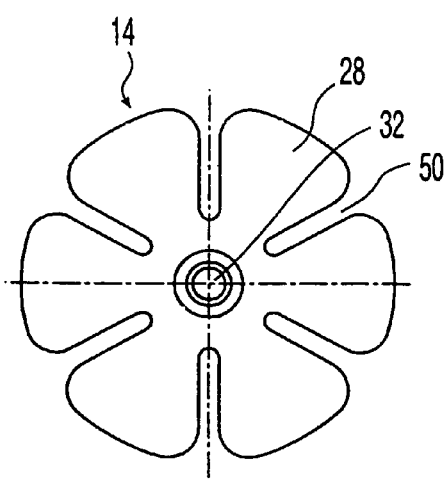
FIG. 3 is a top view of the inner surface of a second clamping member.

In order to minimize the risk of injury to the brain during implantation of cranial flap clamp 10, inner surfaces 18, 28 of first and second clamping members 12, 14 do not have teeth or similar surface features. In other words, inner surfaces 18, 28 are substantially smooth. If the inner surfaces of either or both of first and second clamping members 12, 14 are concave, then movement from the first position to the second position will tend to flatten out the inner surfaces so that more surface area contacts the inferior and/or superior surfaces of bone flap 26 and skull 38. In order to enhance this effect, either or both of first and second clamping member can be provided with radial cutouts. For example, FIG. 3 shows that second clamping member 14 has a plurality of radial cutouts 50 extending radially from opening 32.

Mechanical deformation of extension member 16 near outer surface 30 of second clamping member 14 with first and second clamping members 12, 14 in the second position forms a stop 52 to secure inner surface 18 of first clamping member 12 against inferior surfaces 40, 42 of bone flap 36 and skull 38 and inner surface 28 of second clamping member 14 against superior surfaces 44, 46 of bone flap 36 and skull 38. For cranial flap clamp 10, the mechanical deformation is crimping of extension member 16 near outer surface 30 of second clamping member 14. After the crimping, extension member 16 can be cut to remove any excess that extends substantially above second clamping member 14. Opening 32 of second clamping member 14 can include a countersink 54 (FIG. 3) for receiving stop 52. In an exemplary embodiment, stop 52 fits substantially within countersink 54 (FIG. 5).

FIGS. 6-11 show another embodiment of a cranial flap clamp 110 according to the present invention. Cranial flap clamp 110 includes a first clamping member 112, a second clamping member 114, and an extension member 116. Like cranial flap clamp 10, cranial flap clamp 110 can be made of any suitable biocompatible material, such as stainless steel, titanium, a titanium based alloy, or a resorbable material. If cranial flap clamp 110 is made of a metallic material, preferably first and second clamping members 112, 114 and extension member 116 are made of the same material to minimize the potential for galvanic corrosion. First clamping member 112 has a disk shape with an inner surface 118 and an outer surface 120. Extension member 116 extends from inner surface 118 of first clamping member 112. Although extension member 116 is shown as a ribbon, extension member 116 can be any similar structure so long as the structure and material allow shearing upon twisting against a suitable surface, as explained below.

As shown, extension member 116 is integral with first clamping member 112. Alternatively, extension member 116 can be fastened to first clamping member 112 using any number of known ways. Second clamping member 114 has a disk shape with an inner surface 128 and an outer surface 130 and an opening 132 through inner and outer surfaces 128, 130 for slidably receiving extension member 116. Because opening 132 slidably receives extension member 116, opening 132 and extension member 116 preferably have complimentary shapes. For example, if extension member 116 is a ribbon, then opening 132 preferably has a substantially rectangular shape. In order to prevent second clamping member 114 from sliding off extension member 116, extension member 116 can be provided with a flared proximal portion.

Figure 10:
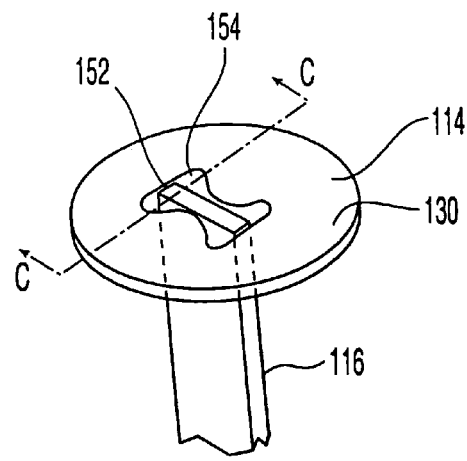
FIG. 10 is a perspective view of the second clamping member of FIG. 7 after twisting and shearing of the extension member.
Figure 11:
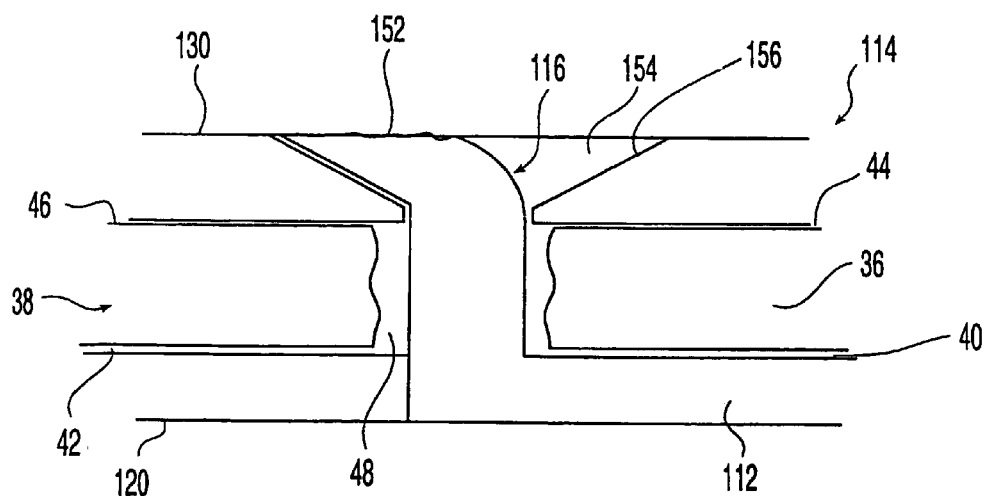
FIG. 11 is a cross sectional view taken along line C-C of FIG. 10 showing the cranial flap clamp implanted.

In use, cranial flap clamp 110 works in a manner analogous to cranial flap clamp 10 and fixes bone flap 36 to skull 38 by drawing first and second clamping members 112, 114 closer together, thereby urging inner surface 118 of first clamping member 112 against inferior surfaces 40, 42 of bone flap 36 and skull 38 and inner surface 128 of second clamping member 114 against superior surfaces 44, 46 of bone flap 36 and skull 38. As best seen in FIGS. 10 and 11, mechanical deformation of extension member 116 near outer surface 130 of second clamping member 114 with first and second clamping member 112, 114 in the second position forms a stop 152 to secure inner surface 118 of first clamping member 112 against inferior surfaces 40, 42 of bone flap 36 and skull 38 and inner surface 128 of second clamping member 114 against superior surfaces 44, 46 of bone flap 36 and skull 38. Second clamping member 114 can be provided with a fastener hole or holes 134 for receiving a fastener, such as a screw, for an additional mechanism to secure second clamping member 114 to bone flap 36 and skull 38.

Figure 8:
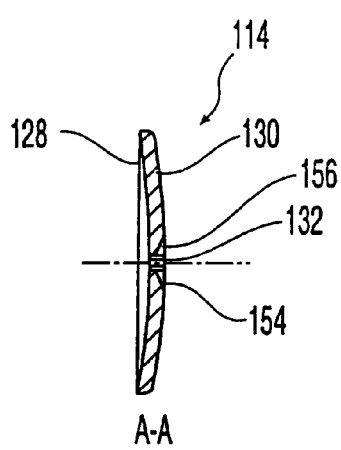
FIG. 8 is a cross sectional view taken along line A-A of FIG. 7.
Figure 9:
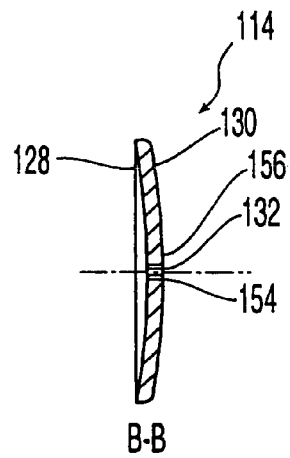
FIG. 9 is a cross sectional view taken along line B-B of FIG. 7.

For cranial flap clamp 110, the mechanical deformation is shearing of extension member 116. In particular, extension member 116 is twisted near outer surface 130 of second clamping member 114 with the first and second clamping members 112, 114 in the second position. A recessed area 154 surrounding opening 132 has edges that form a cutting surface 156 for shearing extension member 116 upon twisting to form stop 152. One geometry to form cutting surface 156 is achieved if recessed area 154 has a width that increases from the center of opening 132 and a depth that also increases from the center of opening 132, as best seen in FIGS. 8 and 9. In an exemplary embodiment, stop 152 fits substantially within recessed area 154 to minimize the profile of cranial flap clamp 110 after implantation.

FIGS. 12-14 show a securing instrument 210 for implantation of the cranial flap clamp according to the present invention. Although instrument 210 can be used with either cranial flap clamp 10, 110, instrument 210 is particularly useful with cranial flap clamp 10. Securing instrument 210 includes first and second handles 212, 214. First and second handles 212, 214 are pivotably connected such that upon squeezing, the distal ends of first and second handles 212, 214 spread apart from each other. A resilient element 216, such as a leaf spring, is located between first and second handles 212, 214 and biases their proximal ends away from each other so that upon releasing of the squeezing pressure, the distal ends of first and second handles 212, 214 pivot back toward each other until contact.

A locking mechanism can be provided to resist the biasing force of resilient element 216. For example, a locking clip 218 is located on second handle 214 and is movable between a free position in which a locking bar 220 is free to move through a channel in locking clip 218 and a ratchet position in which locking bar 220 can only move through locking clip 218 in one direction. This ratchet mechanism allows first and second handles 212, 214 to maintain their relative positions after squeezing and release of the squeezing pressure. In order to create the ratchet effect, a portion of locking bar 220 can be provided with teeth 222 that engage an edge of the channel when locking clip 218 is in the ratchet position.

A gripping arm 224 is operatively connected with first handle 212 and a tensioning arm 226 is operatively connected with second handle 214. Gripping and tensioning arms 224, 226 are movable in response to movement of the first and second handles. Thus, as first and second handles 212, 214 are squeezed, gripping and tensioning arms 224, 226 separate or spread apart from each other.

A slot 228 extends through the distal portions of gripping and tensioning arms 224, 226 for receiving the extension member of the cranial flap clamp. Gripping and tensioning arms 224, 226 can be made as straight extensions from the distal ends of their respective handle. In an exemplary embodiment, however, each of gripping and tensioning arms 224, 226 has a curved body portion with the distal end of securing instrument 210 isolated from the rest of the instrument, so that in use, only the distal end of securing instrument 210 is in contact with the cranium.

A clamping element 230 is operatively associated with slot 228. Clamping element 230 has an inactive configuration in which extension member can freely slide through slot 228 and an active configuration in which a portion of extension member is clamped against a wall of slot 228 to inhibit sliding of the extension member through slot 228. Clamping element 230 includes a clamp 232 rotatably coupled to gripping arm 224. Rotation of clamp 232 within slot 228 upon separation of gripping and tensioning arms 224, 226 moves clamping element 230 from the inactive configuration to the active configuration. A resilient member 234 biases clamping element 230 in the active configuration when gripping and tensioning arms 224, 226 are separated. Tensioning arm 226 includes a foot 236 with a ramped surface maintaining clamping element 230 in the inactive configuration when gripping and tensioning arms 224, 226 are in contact.

In order to crimp the extension member after proper positioning, a crimping assembly 238 is operatively associated with tensioning arm 226. Alternatively, crimping assembly 238 can be associated with gripping arm 224. In an exemplary embodiment, a slider 240 has a crimping edge 242 for crimping the extension member and sides 244 configured and dimensioned for sliding in a grooved end of tensioning arm 226. A link 246 is operatively associated with tensioning arm 226 so that link 246 can slide with respect to tensioning arm 226. Link 246 has a distal end coupled to slider 240 and a proximal end with teeth 248. A lever 250 has a distal end rotatably coupled to tensioning arm 226. The distal end of lever 250 is provided with teeth 252 that engage teeth 248 of the distal end of link 246. As lever 250 is pivoted, the engagement of teeth 248, 252 causes the pivoting to be translated to sliding motion of link 246 and slider 240. A leaf spring or other similar mechanism can be used to cause lever 250 to pivot back. Crimping assembly 238 can also include a cutting stop 254 cooperating with crimping edge 242 of slider 240 to crimp and cut the extension member.

In use, extension member is inserted into slot 228 and securing instrument 210 is moved down toward the cranium with the cranial flap clamp in the position shown in FIG. 4. First and second handles 212, 214 are pivoted to cause gripping and tensioning arms 224, 226 to move away from each other. This movement causes tensioning arm 226 to push against the outer surface of the second clamping member and clamping element 230 to be in the active position, thereby holding the extension member and drawing the first clamping member toward the second clamping member. With the first and second clamping members in the second position; crimping assembly 238 can be used to crimp and cut the extension member.

FIGS. 15-23 show another embodiment of a securing instrument 260 for implantation of the cranial flap clamp 10, 110 according to the present invention. Although instrument 260 may be used with either cranial flap clamp 10, 110, instrument 260 is particularly useful with a resorbable cranial flap clamp 110. Securing instrument 260 may include first and second handles 262, 264, which may be pivotably connected such that upon squeezing, the distal ends 274A, 276A of the instrument 260 may spread apart from each other. As generally described in relation to the embodiment of FIGS. 12-14, the instrument 260 of this embodiment may further comprise a resilient element 266, a locking mechanism provided to resist the biasing force of resilient element 266, and numerous other elements as reference below. These elements may be arranged and operate in the same manner as previously described and thus they will generally not be described in similar detail in relation to the present embodiment.

As shown in FIGS. 15 and 20, tensioning arm 276 and second handle 264 may comprise a unitary member. In contrast, FIG. 12 shows tensioning arm 226 and second handle 214 comprising more than one member, the two of which may be connected by a pin, screw or the like. As in previous embodiments, gripping and tensioning arms 276, 278 may be movable in response to movement of the first and second handles 262, 264. Gripping and tensioning arms 274, 276 may constitute straight extensions from the distal ends of their respective handle. Alternatively, the arms 274, 276 may be curved to provide better access and visualization of the clamping area during use. In an exemplary embodiment, shown in FIGS. 15 and 20, the gripping and tensioning arms 274, 276 may have proximal and distal portions 274A, 274B and 276A, 276B, respectively, with the proximal and distal portions connected by offset portions 274C, 276C. Thus, the distal portions 274B, 276B are offset from the main body 260A of the instrument 260, allowing the distal portion of the instrument to be placed down into the incision while minimizing interference with the edges of the incision. This configuration further ensures that only the distal portion 260B of the instrument 260 may contact the cranium during use.

Figure 17:
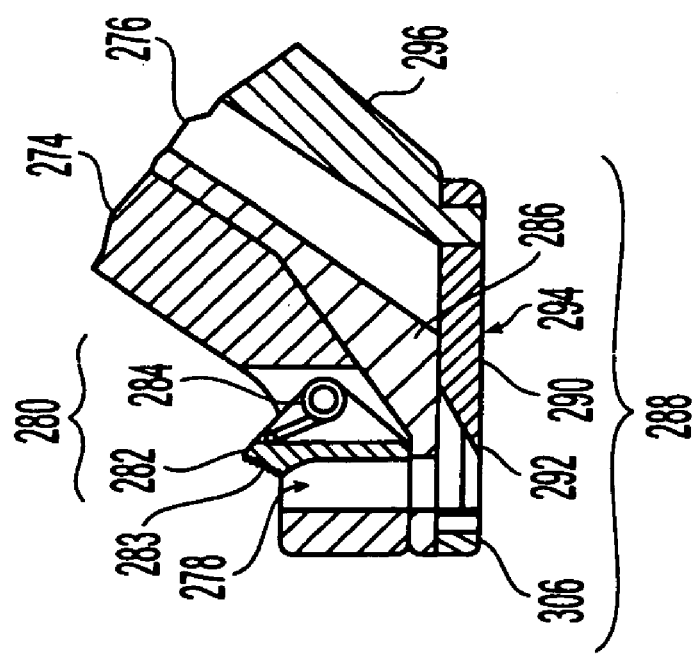
FIG. 17 is a cross sectional view of the distal portion of the securing instrument of FIG. 15.
Figure 23:
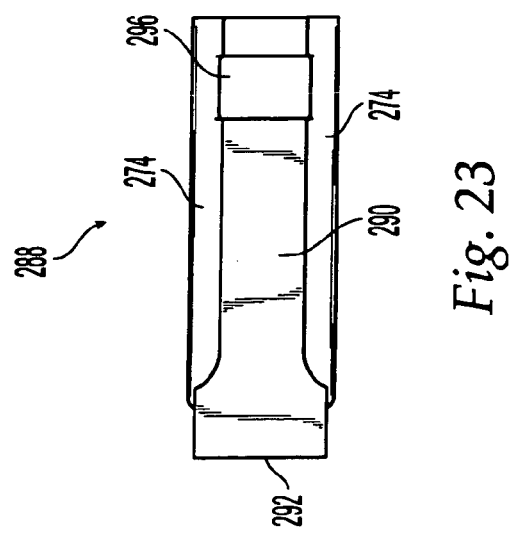
FIG. 23 is a bottom view of the cutting assembly of the instrument of FIG. 15.

Referring to FIG. 17, a clamping element 280 is operatively associated with slot 278. As in previous embodiments, slot 278 may be sized so that the extension member 16, 116 may slide through both the gripping and tensioning arms 274, 276. However, the clamp 282 in this particular embodiment has teeth 283 that may assist in securing the engagement of an extension member 16, 116 in slot 278. Also as in previous embodiments, in order to cut or crimp the extension member 16, 116 after proper positioning, a cutting assembly 288 may be operatively associated with tensioning arm 276 and/or gripping arm 274. The cutting assembly 288 described in relation to this particular embodiment may have all of the components as described above in FIGS. 13 and 14. A bottom view of the cutting assembly 288 is shown in FIG. 23.

Figure 18:
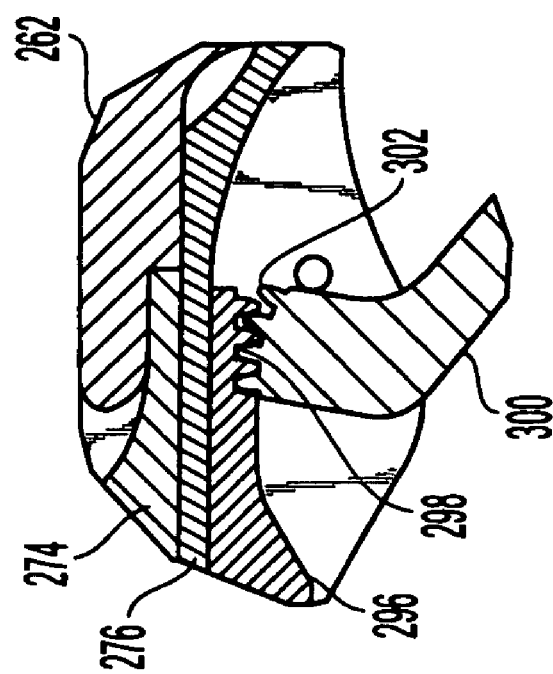
FIG. 18 is a cross sectional view of the proximal portion of the gripping arm of the securing instrument of FIG. 15.
Figure 22:
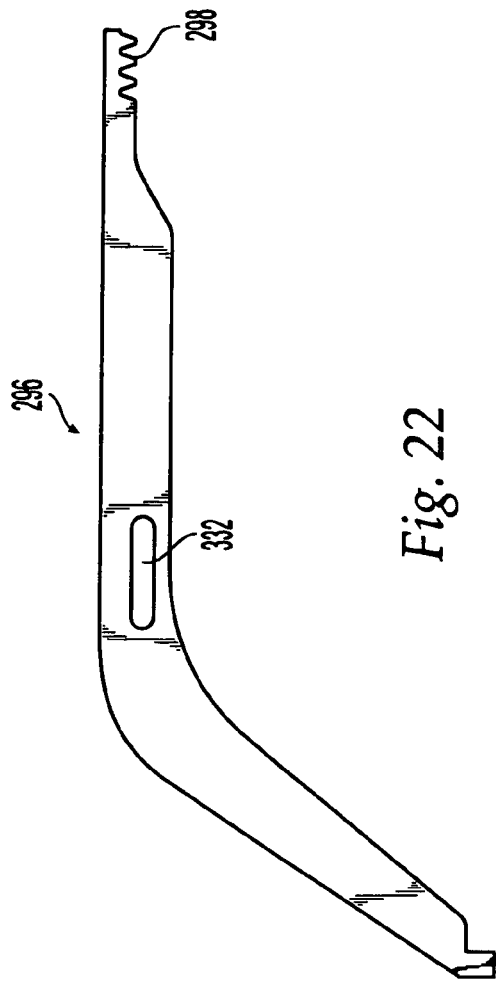
FIG. 22 is a side view of the push arm of the instrument of FIG. 15.
Figure 21:
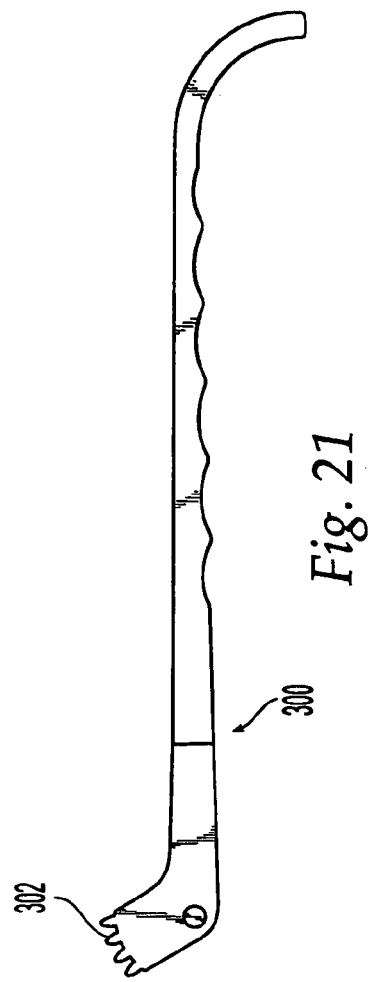
FIG. 21 is a side view of the lever arm of the instrument of FIG. 15.

As in previous embodiments, a lever 300 may also be provided with a distal end rotatably coupled to tensioning arm 276. A detailed view of a lever 300 is shown in FIG. 21. A detailed view of the distal end of a lever 300 is shown in FIG. 18. Further, as seen in FIG. 22, link or push arm 296 may slide along a sliding slot 332 by means of a pin 330.

The tension limiting assembly will now be described in more detail. Referring to FIG. 15, application instrument 260, may include a tension limiting assembly 308, which may be used to prevent the application instrument 260 from over-tensioning and thus damaging a cranial flap clamp 10, 110 during installation. As previously described with respect to the clamp of FIGS. 4 and 5, pulling extension member 16 up while pushing the second clamping member 14 down may result in deformation of the first and second clamping members 12, 14 and an increase in the tensile force in the extension member 16. If the inner surfaces of either or both of the first and second clamping members 12, 14 are concave, then movement from the unclamped to the clamped position may advantageously flatten out the inner surfaces so that more surface area contacts the inferior and/or superior surfaces of bone flap 26 and skull 38. Mechanical deformation of the clamping members 12, 14 may, however, require the application of force to the extension member 16 and second clamping member 14 in excess of the force required to simply move the first and second clamping members 12, 14 toward each other. While it is desirable to apply sufficient force to deform the clamping members 12, 14 so that a maximum surface area of each member contacts the inferior and/or superior surfaces of bone flap 26 and skull 38, it is also desirable to limit the total amount of force applied to the clamping members so as to minimize the chance of damage to the clamping members 12, 14 and/or the extension member 16. This may be of particular importance when installing a cranial flap clamp made of resorbable material, which may be damaged by the application of tensile loads that would otherwise be acceptable in the metal clamp versions. Regardless of the material used for the clamp, however, it will be advantageous to provide an installation tool that will not damage the clamp during installation. Thus, the tension limiting assembly 308 may limit the maximum amount of tensile force that the stepped upper jaw or gripping arm 274 may apply to the extension member 16 and first clamping member 12. This maximum tensile force should be selected to be sufficient to allow the desired seating of the clamping members 12, 14, while being less than a value that could result in undesirable damage to the clamp that would render it unusable or unacceptable for continued use in a patient.

As illustrated in FIGS. 15 and 16, the tension limiting assembly 308 may comprise a tension wire assembly 310 and a breakaway joint 324. The tension wire assembly 310 may include a tension wire 312 having a ball end 314 connected to the gripping arm 274 at a ball end receiving slot 318 and a pin end 316 connected to the first handle 262 at a pin end receiving slot 320. The breakaway joint 324 may comprise a pinned connection disposed between arm 274 and first handle 262 that allows the gripping arm 274 and first handle 262 to be freely pivotable with respect to each other about the joint 324. Since unrestricted pivoting would be undesirable during operation (i.e. it would not allow the transmission of tensioning forces from the first handle 262 to the gripping arm 274, but rather the gripping arm 274 would simply pivot about the joint 324 when the first handle 262 is squeezed toward second handle 264), tension wire 312 is installed between arm 274 and first handle 262 to act as a brace, so that when the first and second handles 262, 264 are squeezed, the gripping and tensioning arms 274, 276 are spread apart in a fashion similar to that described in relation to the instrument of FIG. 12.

The tension-limiting feature lies in providing a tension wire 312 that is at least partially extensible. Thus, when the gripping arm 274 is subjected to a clamping force in excess of a certain predetermined limit, the tension 312 wire may stretch, which in turn may allow the gripping arm 274 to pivot slightly about the break-away joint 324, thereby preventing further clamping movement of the gripping arm 274 away from the tensioning arm 276.

The tension wire 312 may have a first state in which it is substantially longitudinally rigid and a second state in which the wire is longitudinally extensible (i.e. stretchable). The tension wire 312 may assume the first state up to a certain predetermined tensile force, and may transition to the second state when subjected to tensile forces above that predetermined limit. This predetermined force limit may correspond to a maximum allowable force for the cranial flap clamp components.

Thus, in the first state, the wire 312 may hold the handle 262 and gripping arm 274 relatively rigid about the breakaway joint 324, allowing the direct transmission of clamping motion from the first handle 262 to the gripping arm 274 so that the instrument 260 may be used to clamp the components of a cranial flap clamp 10, 100 to the targeted bone segments. In the second state, however, the tension wire 312 may stretch, allowing the gripping arm 274 to pivot about the first handle 262 (i.e. the gripping arm 274 "breaks away" from the first handle 262), thereby preventing the transmission of substantial additional clamping motion from the first handle 262 and the gripping arm 274. In this state, the distal end 274A of the tensioning arm 274 remains substantially stationary with respect to the distal end 274B of the tensioning arm 276, even as the first and second handles 262, 264 are squeezed ever tighter together by the user. Thus, the tension limiting assembly 308 automatically prevents the user from inadvertently applying too high a force to the clamp during installation.

The amount of force required to move stepped upper jaw 276 relative to the first handle 262 about the breakaway joint 324 may be referred to as the breakaway force of the instrument 260. As previously noted, this breakaway force may correspond to a predetermined and/or maximum allowable tensile force that may be applied to the extension member 16, 116 by the gripping and tensioning arms 274, 276 as the cranial flap clamp 10, 110 is secured.

It is noted that tension wire 312 may be connected to the gripping arm 274 and first handle 262 using any suitable end components, or combination of components. For instance, the tension wire 312 may have a first end that is oblong in shape, and a second end that is a cylindrical solid. Further, the tension wire 312 may be attached to the gripping arm 274 and first handle 262 with any suitable attachment structure. Further, instead of a receiving slots 318 and 320, attachment locations may include, but are not limited to, notches, bores, channels, or a combination thereof. The dimensions of an attachment location should correspond to the dimensions of the corresponding end of the tension wire 312.

In use, a cranial flap clamp extension member 16, 116, may be inserted into slot 278 and securing instrument 260 may be moved down toward the cranium with the cranial flap clamp in the position shown in FIG. 4. Referring back to FIG. 15, first and second handles 262, 264 may then be squeezed together to cause gripping and tensioning arms 274, 276 to move away from each other. This movement may cause tensioning arm 276 to push against the outer surface of the second clamping member 14 and clamping element 280 to be in the active position, thereby holding the extension member 16, 116 and pressing the first clamping member 12 toward the second clamping member 14. The tensioning force applied by gripping arm 274 to extension member 16, 116 creates a moment in gripping arm 274 about breakaway joint 324. This moment may initially be counteracted by the tension limiting assembly 308, thus allowing the first handle 262 and gripping arm 274 to operate as a unitary structure about pivot joint 326.

This operation will proceed until the tensioning force applied between the extension member 16, 116 and second clamping member 14 exceeds the predetermined limit of the tension wire 312. Upon the application of additional force, as previously discussed, the tension wire 312 will stretch, allowing gripping arm 274 to pivot about breakaway joint 324, and maintaining the distal end 274A of gripping arm 274 to remain substantially axially stationary with respect to the extension member 16, 116. In this manner, forces exceeding the predetermined limit of the tension wire 312 result in no additional clamping force applied to extension member 16, 116 and second clamping member 14.

The tension limiting assembly 308 may be designed for a specific model or embodiment of a cranial flap clamp 10, 110, so that the maximum application force applied to a particular cranial flap clamp 10, 110 is restricted to a predetermined value that corresponds to the specific model or embodiment. For example, the tension limiting assembly 308 may include a tension wire 312 having super elastic properties and a large region of constant force under increased strain. A nitinol tension wire 312, for instance, having an elongation of about eight percent before rupture may be a suitable tension wire 312 for the tension limiting assembly 308 of FIGS. 15 and 16. Similarly, a stainless steel constant force spring or "negator" spring may be a suitable tension wire 312.

Furthermore, the cross-sectional area of a tension wire 312 may effect the tension limiting properties of the instrument 260. For instance, a tension wire 312 having uniform diameter greater than a second tension wire 312 of uniform diameter will provide greater cross-sectional area and transmit greater tensile force before undergoing super elastic deformation. A nitinol tension wire 312, may therefore have a uniform cross-section that is configured and dimensioned for a cranial flap clamp of a particular size and/or material composition. A non-limiting range of diameters that may be suitable for a nitinol tension wire 312, such as the one shown in the assembly of FIG. 15, may range from about 0.25 mm to about 2.5 mm, which may withstand a maximum tensile force from about 26 N to about 2540 N before super elastic deformation. More particularly, where the instrument of FIG. 15 may be used with a resorbable and/or flexible cranial flap clamp a nitinol tension wire 312 having a diameter of about 0.027 inches may be suitable. A nitinol wire 312 of about 0.027 inches in diameter may have be able to withstand a maximum tensile force of about 191 N before super elastic deformation.

Additionally, the geometry of the tension wire assembly 308 with respect to the central joint 328, may be adjusted to adjust the tension limiting properties of the assembly. For instance, moment M about the central joint 326 equals the tension in the tension wire 312 (i.e., the force acting on gripping arm 274) multiplied by the tangential distance between the tension wire 312 and the central joint 326 (i.e., the length of the gripping arm 274). As the tangential distance of the tension wire 312 from the central joint 326 increases, a smaller force acting on the gripping arm 274 is needed to provide an equivalent moment. Thus, a smaller diameter tension wire 312 may be used to transmit equivalent force to the gripping arm 274. Alternatively, changing the geometry of the tension wire assembly 308 with a given nitinol tension wire 312 may provide different tension limiting properties. For example, a tension wire assembly 308 with a nitinol tension wire 312 having a ball end 314 fixed at a ball end receiving slot 318 on the gripping arm 274 and a pin end 316 that may be selectively fixed at one of multiple pin end receiving slots 320 on the first handle 262 may provide a user with a device having controllably variable tension limiting capabilities. A ball end 314 may be beneficial in that it provides a smaller end for attachment compared to other shaped ends, and subsequently may be inserted in a relatively smaller ball end receiving slot 318. This may be advantageous when the ball end receiving slot 318 is situated in a relatively narrow portion of the instrument 260.

A tension limiting assembly 308 as illustrated in FIG. 15 may also be designed to selectively limit the amount of force applied to a cranial flap clamp 10, 110 within a predetermined range of continuous and/or discrete range of values. Thus, for example, more than one nitinol tension wire 312 may be used to augment the tension limiting capabilities of extension instrument 260. Moreover, where the tension limiting assembly 308 comprises more than one nitinol tension wire 312, each nitinol tension wire 312 may have substantially the same physical and mechanical properties, or two or more of the nitinol tension wires 312 comprising the tension limiting assembly 308 may have different physical and/or mechanical properties. Furthermore, the nitinol tension wire 312 also may be removably secured to the extension instrument 260 so that another nitinol tension wire 312 configured and dimension for a cranial flap clamp of a different size and/or material composition may be used with the extension instrument 260. Thus, for example, two cranial flap clamps of similar size but different material compositions may each have a corresponding nitinol tension wire 312 for use in the tension limiting assembly 308 of FIG. 15.

Tension limiting assembly 308 may further be set with an appropriate factor of safety to ensure, for example, that the extension member 16, 116 of the clamp remains within the proportional limit of the structure, and/or that any yielding by the extension member 16, 116 does not reach an unacceptable level that compromises the integrity of the structure. For instance, one factor of safety may be based on the ratio of the stress at the proportional limit of the post divided by the allowable stress in the post. Such a factor of safety for a resorbable clamp may range from about 1.5 to about 10, while a similar factor of safety for a titanium clamp may range from 1.5 to 10. In one embodiment of the instrument in FIG. 15, the tension limiting assembly 308 may have a factor of safety a value of about 1.5. In another embodiment, the factor of safety may be about 10.

Figure 6:
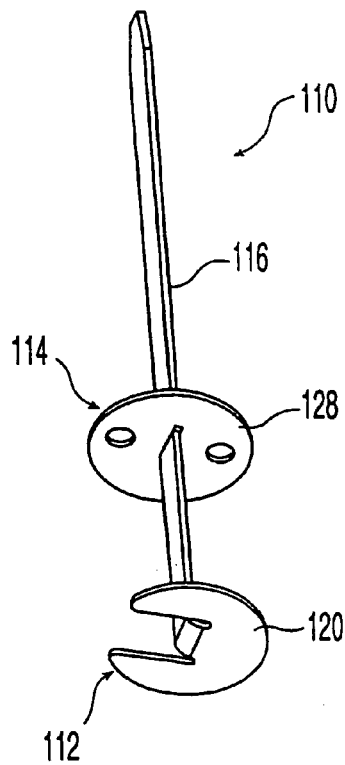
FIG. 6 is a perspective view of another embodiment of a cranial flap clamp according to the present invention.
Figure 7:
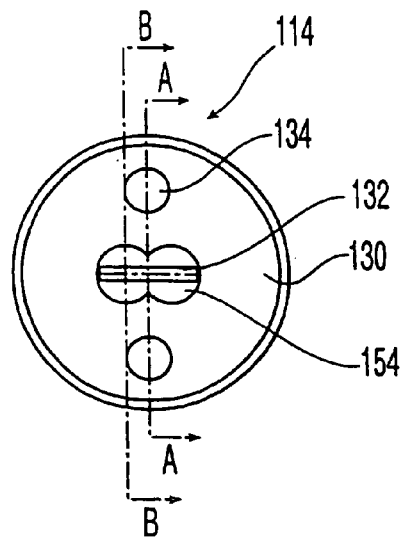
FIG. 7 is a top view of the outer surface of a second clamping member.

Referring to FIG. 19, the first handle 262 of the instrument 260 may have a palm rest 322, which may be configured and adapted to comfortably and securely rest against an anterior portion of a user's hand, so that the user's hand may be used to controllably squeeze the first handle 262 toward the second handle 264. The first handle 262 may also include a structure such as a stop 328 that may provide a surface to oppose sliding of the user's hand toward the distal end of the instrument when either the first handle 262 and second handle 264 are squeezed together or the first handle 262 and the lever arm 300 are squeezed together. Stop 328 also may provide a location for attachment for tension wire 312, which is the pin end receiving slot 320 in embodiment in FIG. 19. The stop 328 may be configured to lie in substantially the same plane as the first and second handles 262, 264, which may facilitate the transfer of forces to the cranial flap clamp along the longitudinal axis of the clamp and in a manner substantially free from torsional loading. For instance, as shown in FIG. 6, second clamping member 114 may be configured to slide with respect to extension member 116 toward the first clamping member 120. Torsional loading of extension member 116 and/or second member 114 may damage structures on either the second member or extension member 116 that may be used to secure the clamp assembly. For example, one or more teeth on the extension member 116 may be configured to interlock with structures contained on or in the second member 114 to lock the assembly. Torsional loading of the extension member 116 may cause the teeth to weaken or deform or break so that the cranial flap clamp may not be reliably secured.

FIG. 19 also shows a pin end receiving slot 320 where a pin end 316 of a tension wire 312 may attach to the first handle 262. A tension wire 312 may pass through a portion of the pin end receiving slot 320 while a pin end 316 is inserted in the slot. First handle 262 may also attach to the lower handle 264 via the central joint 326, and may further attach to gripping arm 274 via breakaway joint 324. First handle 262 may also have a through-bore 334B to correspond with through-bore 334A in gripping arm 274 (see FIG. 15) to form a common bore 334. A pin (not shown) or other equivalent structure may be inserted into the common bore 334 to prohibit the distal ends 274A, 276A of the gripping arm 274 and tensioning arm 276 from separating when the first and second handles 262, 264 are actuated.

Another embodiment of an instrument 260 having a tension limiting assembly 308 is shown in FIGS. 24A-25B. In this embodiment, the tension limiting assembly 308 may comprise a cantilever beam 350. The cantilever beam 350 may have a proximal end 352 and a distal end 354, with a humped body 356 extending therebetween. Beam 350 may also have a central bore 358 and a distal bore 360. Body 356 may be generally curved to more effectively distributes stress loads upon the beam 350 during use. Beam 350 may also be appropriately shaped to effectively accommodate the shape of an adjacent component of instrument 260. Beam 350 may be made out of a suitable metal or alloy, such as stainless steel.

Figure 24A:
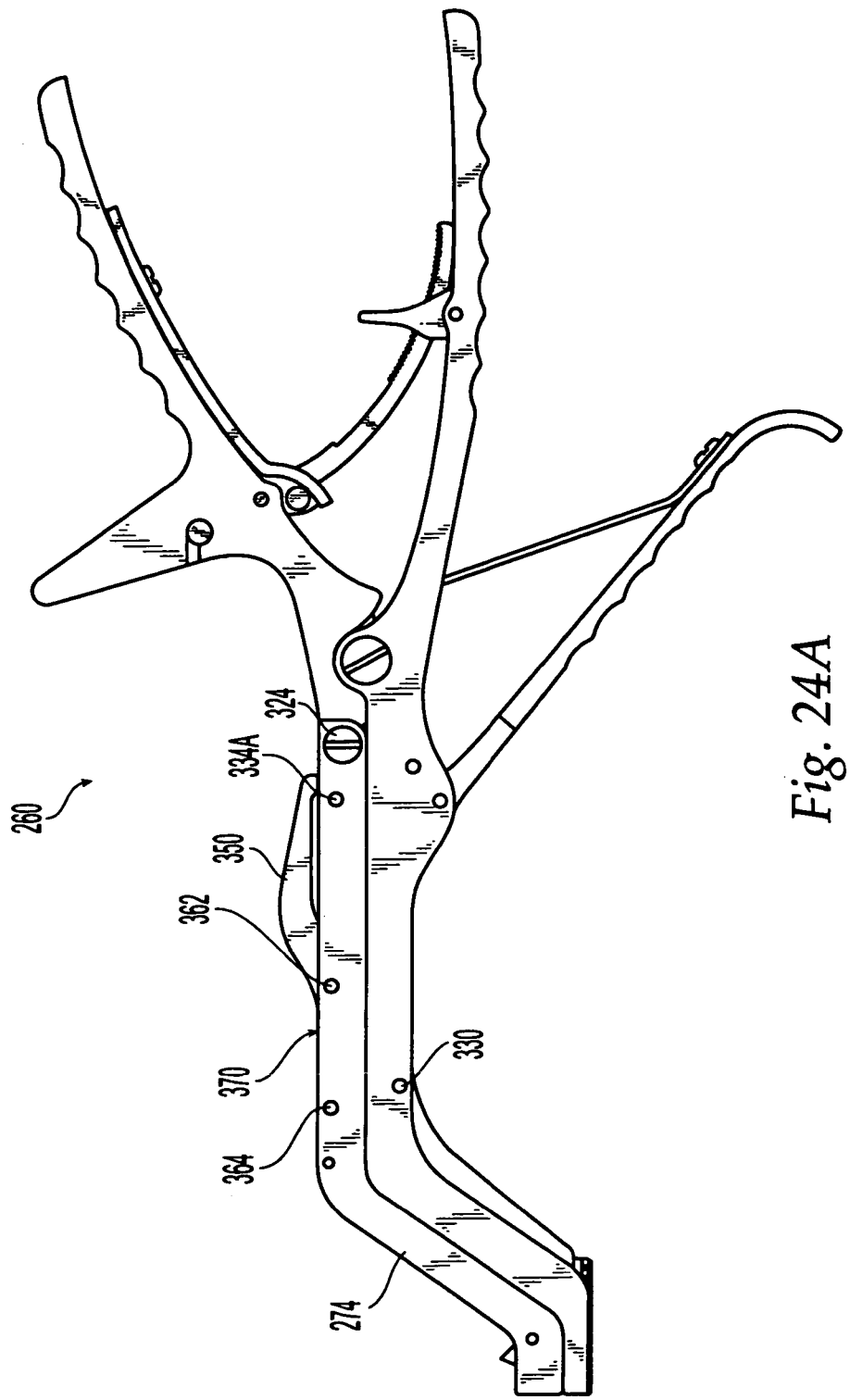
FIG. 24A is a side view of another embodiment of a securing instrument having a cantilever beam tension limiting assembly.

In use, beam 350 may be placed in engagement with gripping arm 274, which may occur in slot 370, as shown in FIGS. 24A-24B. Gripping arm 274 may have primary beam bores 362, 364, which may be aligned with central bore 358 and distal bore 360, respectively. Beam securing pins 366, 368 may be inserted through central bore 358 via primary beam bore 362, and through distal bore 360 via primary beam bore 364, respectively.

Functionally, a tension limiting assembly 308 utilizing a cantilever beam 350 may be substantially identical to an assembly 308 utilizing a tension wire 312. Generally, as first and second handles 262, 264 may be squeezed together to cause gripping and tensioning arms 274, 276 to move away from each other, the tensioning force applied by gripping arm 274 to an extension member 16, 116 may create a moment in gripping arm 274 about breakaway joint 324. Such force interactions are discussed in more detail above. As a tension wire 312 serves to counteract and/or distribute forces on the gripping arm 274, similarly so may a cantilever beam 350 used as discussed above. It should also be mentioned that a single instrument 260 may utilize a tension wire 312 and a cantilever beam 350 interchangeably.

The invention described and claimed herein is not to be limited in scope by the specific embodiments herein disclosed, since these embodiments are intended solely as illustrations of several aspects of the invention. Any equivalent embodiments are intended to be within the scope of this invention. Indeed, various modifications of the invention in addition to those shown and described herein will become apparent to those skilled in the art from the foregoing description. It is envisioned that the tension limiting properties of the application instrument may be useful for other surgical instruments, hand tools, or other mechanical applications where it may be desirable to transmit near constant forces to an object or work piece. Such modifications are also intended to fall within the scope of the appended claims.

What is claimed:

1. A securing instrument for a cranial flap clamp comprising:
   first and second handles pivotally associated with each other;
   a gripping arm, and a tensioning arm, the gripping arm operatively associated with the first handle and the tensioning arm operatively associated with the second handle; the gripping and tensioning arms being movable in response to movement of the first and second handles;
   the gripping and tensioning arms each further having proximal and distal portions, the distal portions each having a recess extending therethrough configured to receive an extension member of the cranial flap clamp;
   a clamping assembly operatively associated with the recess and having an inactive configuration in which the clamping assembly allows the extension member to slide in the recess, and an active configuration in which the assembly fixes the extension member in the recess; and
   a crimping element operatively associated with at least one of the gripping and tensioning arms, the crimping element configured to crimp the extension member, the crimping element further having first and second crimping members;
   wherein squeezing the first and second handles together configures the clamping assembly to the active configuration.

2. The securing instrument of claim 1, the clamping element further comprising a clamp rotatably coupled to the gripping arm, such that separating the gripping and tensioning arms rotates the clamp within the recess and moves the clamping element from the inactive configuration to the active configuration.

3. The securing instrument of claim 2, further comprising a resilient member disposed between the first and second handles for biasing the clamping element in the active configuration when the gripping and tensioning arms are separated.

4. The securing instrument of claim 3 wherein the tensioning arm further comprises a foot operative to maintain the clamping elements in the inactive configuration when the gripping and tensioning arms are in contact.

5. The securing instrument of claim 4 wherein the foot includes a ramped surface for engaging the clamping element to fix the extension member within the recess.

6. The securing instrument of claim 1, wherein:
   the distal portion of the tensioning arm further includes a grooved end,
   the crimping assembly further comprises:
   a slider having a crimping edge for crimping the extension member, and sides configured and dimensioned to slidably engage with the grooved end of the tensioning arm;
   a link operatively associated with the tensioning arm for sliding movement with respect thereto, the link having a distal end coupled to the slider and a proximal end comprising teeth; and
   a lever rotatably coupled with the tensioning arm, the lever having a proximal gripping portion and a distal portion comprising teeth configured to engage the teeth of the link;
   wherein moving the lever in a first direction with respect to the tensioning arm causes the crimping edge of the slider to crimp an extension member placed therein.

7. The securing instrument of claim 6 wherein the crimping assembly further includes a cutting stop, the cutting stop configured to cooperate with the crimping edge of the slider to at least crimp the extension member.

8. The securing instrument of claim 1, wherein:
the gripping arm further comprises an intermediate portion located between the gripping arm proximal and distal portions, the gripping arm proximal portion associated with the distal portion of the first handle, the distal portion of the gripping arm extending from the intermediate portion substantially parallel to the proximal portion, and the intermediate portion angled with respect to the gripping arm proximal and distal portions;
the tensioning arm further comprises an intermediate portion located between the tensioning arm proximal and distal portions; the tensioning arm proximal portion associated with the distal portion of the second handle, the distal portion of the tensioning arm extending from the intermediate portion substantially parallel to the proximal portion, and the intermediate portion angling from the tensioning arm proximal portion;
wherein the intermediate portions of the gripping and tensioning arms are oriented substantially parallel when the instrument is in the inactive configuration.

9. The securing instrument of claim 1 further comprising a resilient element associated with the first and second handles to bias the first and second handles away from each other.

10. The securing instrument of claim 9 further comprising a locking bar having a first end pivotably coupled to the first handle and a curved body portion with a plurality of teeth; and a locking clip pivotably coupled to the second handle and having a through channel, wherein the locking clip is movable between a free position in which the locking bar is moveable within the channel and a ratchet position in which the teeth of the locking bar engage a surface of the channel to prohibit the locking bar from moving with respect to the channel, thereby locking the relative positions of the first and second handles with respect to each other.

11. The securing instrument of claim 1, further comprising a tension limiting assembly, comprising an extendable tension element having first and second ends, the first end releasably attachable to the first handle at a first location and the second end releasably attachable to the gripping arm; wherein the first handle and the gripping arm are connected at a pivot joint.

12. The securing instrument of claim 11, wherein the first and second ends of the extensible tension element engage the first handle and the gripping arm to allow the handle and arm to pivot with respect to each other in a first direction and to resist pivoting in the opposite direction.

13. The securing instrument of claim 12, wherein the tension element resists pivoting of the handle and arm in the first direction until about 15 newtons (N) is applied to the distal portion of the gripping arm via the handles.

14. The securing instrument of claim 13, wherein when a force greater than about 15 N is applied via the handles to the distal portion of the gripping arm, the tension element stretches to allow the handle and arm to pivot in the first direction.

15. The securing instrument of claim 14, wherein after the handle and arm pivot in the first direction, further force applied via the handles to the distal portion of the gripping arm causes the tension element to stretch, with substantially no additional force transmitted to the cranial flap clamp.

16. The securing instrument of claim 11, wherein the tension element comprises a nitinol wire having a diameter of from about 0.25 mm to about 2.5 mm.

17. The securing instrument of claim 16, wherein the nitinol wire has a maximum strain of about 5% to about 11% before rupture.

18. The securing instrument of claim 11, wherein at least one of the first and second ends of the tension element comprises a ball end.

19. The securing instrument of claim 11, wherein at least one of the first and second ends of the tension element comprises a pin end.

20. The securing instrument of claim 11, further comprising a second tension element having first and a second ends, each end having an attachment element, wherein the first end is attachable at the first handle and the second end is attachable to the gripping arm.

21. The securing instrument of claim 20, wherein at least one tension element comprises a nitinol wire.

22. The securing instrument of claim 20, wherein the first and second tension elements have substantially different compositions.

23. The securing instrument of claim 20, wherein the first and second tension wires have substantially different tensile strengths.

24. The securing instrument of claim 20, wherein the first and second tension wires have substantially different cross-section diameters.

25. The securing instrument of claim 1, further comprising a tension limiting assembly comprising a cantilever beam, wherein the cantilever beam is releasably attachable to the gripping arm.

26. The securing instrument of claim 25, wherein the cantilever beam is substantially curved.

27. The securing instrument of claim 25, wherein the cantilever beam is comprised of stainless steel.

28. A kit for use with a cranial flap clamp, comprising:
the securing instrument of claim 1;
a plurality of tension elements, at least one tension element having a first and second end, the first end having an attachment element for engaging the first arm and the second end having an attachment element for engaging the gripping arm;
wherein at least two of the plurality of tension elements have force/strain ratios that are substantially unequal.

29. The kit of claim 28, wherein at least one tension element comprises a nitinol wire.

30. The kit of claim 28, wherein at least two of the plurality of tension elements are comprised of substantially the same material.

31. The kit of claim 28, wherein at least one of the plurality of tension elements comprises a nitinol wire and a second of the plurality of tension elements comprises a constant-force spring.

32. The kit of claim 28, wherein at least two of the plurality of tension elements have substantially different tensile strengths.

33. The kit of claim 28, wherein at least one of the plurality of tension elements is a cantilever beam.

34. A securing instrument for a cranial flap clamp comprising:
a first handle associated with a first clamping arm and a second handle associated with a second clamping arm, the first and second handles being pivotally connected;
the first and second clamping arms each further having a distal portion, the distal portions each further defining a respective recess that is configured to receive at least a portion of an extension element of the cranial flap clamp;
an extension element-clamping assembly operatively associated with the recess of the first clamping arm; the assembly configured to selectively secure the extension element;

a clamp-engaging surface associated with the second clamping arm, the clamp-engaging surface configured to contact a clamp member of the cranial flap clamp; and a crimping assembly associated with the second arm and configured to at least partially deform the extension element;

wherein when the extension element-clamping assembly secures the extension element and the clamp-engaging surface contacts the clamp surface, moving the handles with respect to each other causes the clamp member to slide along the extension element.

35. The securing instrument of claim 34, the crimping assembly further comprising first and second crimping members disposed near the distal end of the second arm and configured to actuate when the first and second handles are urged together.

36. The securing instrument of claim 35, wherein moving the first and second handles together causes the extension element engaging assembly to secure the extension element, and causes the first and second crimping members to crimp the extension member.

37. The securing instrument of claim 36, wherein the crimping assembly further includes a cutting element configured to cooperate with at least one of the crimping members to at least crimp the extension member.

38. The securing instrument of claim 34, the extension element-engaging clamping assembly further comprises a gripping element disposed within the recess of the first clamping arm, and rotatably coupled to the first clamping arm such that moving the first and second handles rotates the gripping element within the recess to selectively secure the extension element.

39. The securing instrument of claim 34, the first and second arms further comprising a handle-engaging portion associated with the first and second handles, respectively, and an intermediate portion disposed between the handle-engaging and distal portions, the intermediate portions oriented at an oblique angle with respect to their respective distal portions.

40. The securing instrument of claim 34, further comprising a tension limiting assembly, comprising an extendable tension element having first and second ends, the first end releasably attachable to the first handle at a first location and the second end releasably attachable to the first clamping arm; wherein the first clamping arm is pivotably associated with the first handle.

41. The securing instrument of claim 40, the first clamping arm and first handle connected via a pivot joint, wherein the first and second ends of the extensible tension element engage the first handle and the first clamping arm to allow the handle and arm to pivot with respect to each other in a first direction about the pivot joint and to resist pivoting in the opposite direction about the pivot joint.

42. The securing instrument of claim 41, wherein the tension element resists pivoting of the handle and arm in the first direction until about 15 N is applied to the distal portion of the gripping arm via the handles.

43. The securing instrument of claim 41, wherein when a force greater than about 15 N is applied via the handles to the distal portion of the gripping arm, the tension element stretches to allow the handle and arm to pivot in the first direction.

44. The securing instrument of claim 43, wherein after the handle and arm pivot in the first direction, further force applied via the handles to the distal portion of the gripping arm causes the tension element to stretch, with substantially no additional force transmitted to the cranial flap clamp.

45. The securing instrument of claim 44, wherein the tension element comprises a nitinol wire.

46. The securing instrument of claim 45, wherein the nitinol wire has a diameter of from about 0.25 mm to about 2.5 mm.

47. The securing instrument of claim 45, wherein the nitinol wire has a maximum strain of about 5% to about 11% before rupture.

48. The securing instrument of claim 40, wherein at least one of the first and second ends of the tension element comprises a ball end.

49. The securing instrument of claim 40, wherein at least one of the first and second ends of the tension element comprises a pin end.

50. The securing instrument of claim 40, the tension limiting assembly further comprising a second tension element having first and a second ends, each end having an attachment element, wherein the first end is attachable at the first handle and the second end is attachable to the first clamping arm.

51. The securing instrument of claim 50, wherein the first and second tension elements have substantially different compositions.

52. The securing instrument of claim 51, wherein the first and second tension wires have substantially different tensile strengths.

53. The securing instrument of claim 40, wherein at least one tension element comprises a nitinol wire.

54. The securing instrument of claim 34, further comprising a tension limiting assembly comprising a cantilever beam, wherein the cantilever beam is releasably attachable to the gripping arm.

55. The securing instrument of claim 54, wherein the cantilever beam is substantially curved.

56. The securing instrument of claim 54, wherein the cantilever beam is comprised of stainless steel.

57. A cranial flap clamp system comprising:
at least one cranial flap clamp comprising first and second skull clamping elements and an extension element configured to connect the clamping elements; and
a cranial flap clamp installation instrument including:
a first handle associated with a first clamping arm and a second handle associated with a second clamping arm, the first and second handles being pivotally connected, the first and second clamping arms each further having a distal portion, the distal portions each further configured to receive at least a portion of an extension element of the cranial flap clamp;
an extension element-clamping assembly operatively associated with the distal portion of the first clamping arm; the assembly configured to selectively secure the extension element; and
a clamp-engaging surface associated with the second clamping arm, the clamp-engaging surface configured to contact one of the first and second skull clamping elements;
a crimping assembly associated with the second arm and configured to at least partially deform the extension element;
wherein when the extension element-clamping assembly secures the extension element and the clamp-engaging surface contacts the clamp surface, moving the handles with respect to each other causes the extension element and the clamp surface to move with respect to each other.

58. The cranial flap clamp system of claim 57, the crimping assembly further comprising a slider having a crimping edge, the crimping edge configured to crimp an extension member placed within the recess.

59. The cranial flap clamp system of claim 58, wherein moving the first and second handles together causes the extension element engaging assembly to secure the extension element.

60. The cranial flap clamp system of claim 59, wherein the crimping assembly further includes a cutting element configured to cooperate with at least one of the crimping members to at least crimp the extension member.

61. The cranial flap clamp system of claim 57, the extension element-engaging clamping assembly further comprises a gripping element disposed within the recess of the first clamping arm, and rotatably coupled to the first clamping arm such that moving the first and second handles rotates the gripping element within the recess to selectively secure the extension element.

62. The cranial flap clamp system of claim 57, the first and second arms further comprising a handle-engaging portion associated with the first and second handles, respectively, and an intermediate portion disposed between the handle-engaging and distal portions, the intermediate portions oriented at an oblique angle with respect to their respective distal portions.

63. The cranial flap clamp system of claim 57, further comprising a tension limiting assembly, comprising an extendable tension element having first and second ends, the first end releasably attachable to the first handle at a first location and the second end releasably attachable to the first clamping arm; wherein the first clamping arm is pivotably associated with the first handle.

64. The cranial flap clamp system of claim 63, the first clamping arm and first handle connected via a pivot joint, wherein the first and second ends of the extensible tension element engage the first handle and the first clamping arm to allow the handle and arm to pivot with respect to each other in a first direction about the pivot joint and to resist pivoting in the opposite direction about the pivot joint.

65. The cranial flap clamp system of claim 64, wherein at least a portion of the cranial flap clamp is comprised of a bioresorbable material.

66. The cranial flap clamp system of claim 65, wherein the tension element resists pivoting between the handle and arm in the first direction until about 15 N is applied between the distal portions of the gripping and tensioning arms using the handles.

67. The cranial flap clamp system of claim 66, wherein when about 15 N is applied between the distal portions of the gripping and tensioning arms, further movement of the handles together causes the tension element to stretch, with substantially no additional force transmitted to the cranial flap clamp.

68. The cranial flap clamp system of claim 67, wherein the tension element comprises a nitinol wire.

69. The cranial flap clamp system of claim 68, wherein the nitinol wire has a diameter of from about 0.25 mm to about 2.5 mm.

70. The cranial flap clamp system of claim 68, wherein the nitinol wire has a maximum strain of about 5% to about 11% before rupture.

71. The cranial flap clamp system of claim 65, wherein when a force greater than about 15 N is applied via the handles between the distal portions of the gripping and tensioning arms, the tension element stretches to allow the handle and arm to pivot in the first direction.

72. The cranial flap clamp system of claim 64, wherein at least a portion of the cranial flap clamp is comprised of metal.

73. The cranial flap clamp system of claim 72, wherein the metal is titanium.

74. The cranial flap clamp system of claim 63, wherein at least one of the first and second ends of the tension element comprises a ball end.

75. The cranial flap clamp system of claim 63, wherein at least one of the first and second ends of the tension element comprises a pin end.

76. The cranial flap clamp system of claim 63, the tension limiting assembly further comprising a second tension element having first and a second ends, each end having an attachment element, wherein the first end is attachable at the first handle and the second end is attachable to the first clamping arm.

77. The cranial flap clamp system of claim 57, further comprising a tension limiting assembly comprising a cantilever beam, wherein the cantilever beam is releasably attachable to the gripping arm.

78. The cranial flap clamp system of claim 77, wherein the cantilever beam is substantially curved.

79. The cranial flap clamp system of claim 77, wherein the cantilever beam is comprised of stainless steel.

80. A securing instrument for a cranial flap clamp having first and second clamp members and an extension element connected to the first clamp member and extending beyond the second clamp member, the securing instrument comprising:
  a first handle associated with a first clamping arm and a second handle associated with a second clamping arm, the first and second handles being movably connected to each other;
  the first and second clamping arms each further having a distal portion, the distal portions each further defining a respective recess that is configured to receive at least a portion of the extension element;
  an extension element-clamping assembly operatively associated with the recess of the first clamping arm, the extension element-clamping assembly including a clamping element coupled to the first clamping arm and a resilient member configured to bias against the clamping element, and the extension element-clamping assembly configured to selectively secure the extension element such that 1) when the distal portions of the first and second clamping arms move toward each other, the second clamping arm biases the resilient member away from the clamping element, and 2) when the distal portions of the first and second clamping arms move away from each other, the resilient member biases the clamping element into contact with the extension element thereby securing the extension member with respect to sliding relative to the first clamping arm; wherein
  the second clamping arm carries a clamp-engaging surface that is configured to contact a the second clamp member, such that when the extension element-clamping assembly secures the extension element and the clamp-engaging surface contacts the second clamp member, moving the handles with respect to each other causes the second clamp member to slide along the extension element toward the first clamp member.

81. A securing instrument for a cranial flap clamp comprising:
  a first handle associated with a first clamping arm and a second handle associated with a second clamping arm, the first and second handles being movably connected to each other;

the first and second clamping arms each 1) having a distal portion and 2) extending along a direction of elongation from their respective distal portions to the first and second handles, the first and second clamping arms each further defining a respective recess configured to receive at least a portion of an extension element of the cranial flap clamp such that the extension element extends through the recess in a direction that is angularly offset with respect to the direction of elongation;

an extension element-clamping assembly operatively associated with the recess of the first clamping arm and configured to selectively secure the extension element; and a clamp-engaging surface associated with the second clamping arm, the clamp-engaging surface configured to contact a clamp member of the cranial flap clamp;

wherein when the extension element-clamping assembly secures the extension element and the clamp-engaging surface contacts the clamp surface, moving the handles with respect to each other causes the clamp member to slide along the extension element.

82. The securing instrument of claim 81 further comprising a crimping element operatively associated with at least one of the gripping and tensioning arms, the crimping element configured to crimp the extension member.

83. The securing instrument of claim 81, wherein the direction in which the extension element extends through the recess is a direction transverse to the direction of elongation.

* * * * *